US011661458B2

(12) United States Patent
Zippel et al.

(10) Patent No.: US 11,661,458 B2
(45) Date of Patent: May 30, 2023

(54) ANTI-NRP1A ANTIBODIES AND THEIR USES FOR TREATING EYE OR OCULAR DISEASES

(71) Applicant: Boehringer Ingelheim International GmbH, Ingelheim am Rhein (DE)

(72) Inventors: Nina Zippel, Biberach an der Riss (DE); Pankaj Gupta, Scarsdale, NY (US); Fei Han, Sandy Hook, CT (US); Sarah Low, Carmel, NY (US); Juergen Prestle, Biberach an der Riss (DE); Leo Thomas, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/030,421

(22) Filed: Sep. 24, 2020

(65) Prior Publication Data

US 2021/0087282 A1    Mar. 25, 2021

(30) Foreign Application Priority Data

Sep. 24, 2019 (EP) .................................... 19199099
Jan. 9, 2020 (EP) .................................... 20150942

(51) Int. Cl.
| | | |
|---|---|---|
| *C07K 16/28* | (2006.01) | |
| *A61P 27/02* | (2006.01) | |
| *C12N 15/63* | (2006.01) | |
| *A61K 9/00* | (2006.01) | |

(52) U.S. Cl.
CPC ........ *C07K 16/2863* (2013.01); *A61K 9/0019* (2013.01); *A61P 27/02* (2018.01); *C12N 15/63* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,419,446 A | 12/1983 | Howley et al. |
| 4,496,689 A | 1/1985 | Mitra |
| 4,560,655 A | 12/1985 | Baker |
| 4,601,978 A | 7/1986 | Karin |
| 4,640,835 A | 2/1987 | Shimizu et al. |
| 4,657,866 A | 4/1987 | Kumar |
| 4,670,417 A | 6/1987 | Iwasaki et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,631,144 A | 5/1997 | Lemoine et al. |
| 5,888,809 A | 3/1999 | Allison |
| 6,037,454 A | 3/2000 | Jardieu et al. |
| 6,054,297 A | 4/2000 | Carter et al. |
| 6,407,213 B1 | 6/2002 | Carter et al. |

FOREIGN PATENT DOCUMENTS

| | | |
|---|---|---|
| AU | 2011253904 A1 | 1/2012 |
| DK | 266710 A | 4/1989 |
| EP | 183070 A2 | 6/1986 |
| EP | 0244234 A2 | 11/1987 |
| EP | 0402226 A1 | 12/1990 |
| EP | 3241844 A1 | 11/2017 |
| WO | 198700195 A1 | 1/1987 |
| WO | 199003430 A1 | 4/1990 |
| WO | 199013646 A1 | 11/1990 |
| WO | 199411026 A2 | 5/1994 |
| WO | 199632478 A1 | 10/1996 |
| WO | 2007056470 | 5/2007 |
| WO | 2008143666 A2 | 11/2008 |
| WO | 2014127479 | 8/2014 |
| WO | 2016033699 | 3/2016 |
| WO | 2018119171 | 6/2018 |

OTHER PUBLICATIONS

Liang et al. J. Mol. Biol. 366: 815-829, 2007.*
Seongbeom, IDBooo62, a dual targeting protein for enhanced anti-angiogenic effect for several ocular diseases, ARVO Journals, 2019.
Almagro, Juan C. et al. "Antibody modeling assessment", (2011) Proteins, 79(11), 3050-3066.
Altschul, Stephen F. et al. "Basic Local Alignment Search Tool" (1990) J. Mol. Biol., vol. 215, 403-410.
Altschul, Stephen F. et al. "Gapped BLAST and PSI-BLAST: a new generation of protein database search programs" (1997) Nucleic Acids Research, vol. 25(17) 3389-3402.
Bakri, Sophie et al. "Pharmacokinetics of Intravitreal Bevacizumab (Avastin)" (2007) Opthalmology, 855-859.
Barnes, David, et al. "Methods for Growth of Cultured Cells in Serum-Free Medium" (1980) Analytical Biochemistry, vol. 102, 255-270.
Brennan, Maureen et al., "Preparation of Bispecific Antibodies by Chemical Recombination of Monoclonal Immunoglobulin G1 Fragments", (1985) Science, vol. 229, Issue 4708, 81-83.
Carter, Paul, et al. "High level *Escherichia Coli* Expression and Production of a Bivalent Humanized Antibody Fragment" (1992) Biotechnology, vol. 10, 163-167.
Chothia, Cyrus et al. "Canonical Structures for the Hypervariable Regions of Immunoglobulins" (1987) J. Mol. Biol., vol. 196, 901-917.
Chothia, Cyrus et al. (1985) "Domain Association in Immunoglobulin Molecules The Packing of Variable Domains" J. Mol. Biol. 186, 651-663.

(Continued)

*Primary Examiner* — Christine J Saoud
(74) *Attorney, Agent, or Firm* — Kenneth J. Kalafus

(57) ABSTRACT

Disclosed are antibodies and fragments thereof that target the A-domain of Neuropilin-1 (Nrp1A). Also disclosed are methods of using the anti-Nrp1A antibodies for the treatment of various diseases or disorders.

35 Claims, 8 Drawing Sheets
Specification includes a Sequence Listing.

(56) References Cited

OTHER PUBLICATIONS

Clackson, Tim et al. "Making antibody fragments using phage display libraries", (1991) Letters to Nature, vol. 352, 624-628.
De Groot, Anne S. et al. Activation of natural regulatory T cells by IgG Fc-derived peptide "Tregitopes" (2008) Blood, vol. 112(8), 3303-3311.
De Groot, Anne S. et al. "Reducing risk, improving outcomes : Bioengineering less immunogenic protein therapeutics" (2009) Clinical Immunology, vol. 131,189-201.
Edge, Albert S. B. et al., "Deglycosylation of glycoproteins by trifluoromethanesulfonic acid" (1981)Analytical Biochemistry, vol. 118, 131-137.
Fleer, R., et al. "Stable Multicopy Vectors for High-Level Secretion of Recombinant Human Serum Albumin by Kluyveromyces Yeasts" (1991) Biotechnology, vol. 9(10), 968-975.
Graham, F., L., et al. " Characteristics of a Human Cell Line Transformed by DNA from Human Adenovirus Type 5" (1977) J. Gen. Virol., vol. 36, 59-74.
Guss, Bengt, et al. "Structure of the IgG-binding regions of streptococcal protein G"(1986) EMBO Journal, vol. 5(7), 1567-1575.
Ham, Richard G., et al. "Media and Growth Requirements", (1979) Methods in Enzymology, vol. 58, pp. 44-93.
Higgins, D. G., et al."Using Clustal for Multiple Sequence Alignments" (1996) Methods in Enzymology, vol. 266, 383-402.
Hutton-Smith, Laurence A. et al., "A Mechanistic Model of the Intravitreal Pharmacokinetics of Large Molecules and the Pharmacodynamic Suppression of Ocular Vascular Endothelial Growth Factor Levels by Ranibizumab in Patients with Neovascular Age-Related Macular Degeneration" (2016) Molecular Pharmaceutics, vol. 13, 2941-2950.
European Patent Office, International Search Report and Written Opinion (ISA/EP) for PCT/EP2020/076685, dated Jan. 12, 2021, 19 pgs.
Jawa, Vibha et al. "T-cell dependent immunogenicity of protein therapeutics: Preclinical assessment and mitigation", (2013) Clinical Immunology, vol. 149, 534-555.
Jones, Elizabeth et al, "Proteinase Mutants of Saccharomyces Cerevisiae" (1977) Genetics, 85: 12, 23-33.
Kabat, et al. "Sequences of Proteins of Immunological Interest", (1991) U.S. Department of Health and Human Services, vol. I, 5th Edition, 25 pgs.
Karlin, Samuel et al. "Methods for assessing the statistical significance of molecular sequence features by using general scoring schemes" (1990) Proc. Natl. Acad. Sci. USA, vol. 87, 2264-2268.
Karlin, Samuel et al. "Applications and statistics for multiple high-scoring segments in molecular sequences" (1993) Proc Natl Acad Sci. USA, vol. 90, 5873-5877.
Kohler, G. et al. "Continuous Cultures of Fused Cells Secreting Antibody of Predefined Specificity" (1975) Nature, vol. 256, 495-497.
Lindmark, Roger, et al. "Binding of Immunoglobulins to Protein A and Immunoglobulin levels in Mammalian Sera" (1983) Journal Immunological Methods, vol. 62, 1-13.
Maier, Johannes et al. "Assessment of fully automated antibody homology modeling protocols in molecular operating environment"(2014), Proteins, 82(8), 1599-1610.

Marks, James D., et al., "By-passing immunization : Human antibodies from V-gene Libraries Displayed on Phage", (1991) J. Mol. Biol., vol. 222, 581-597.
Mather, Jennie P. "Establishment and Characterization of Two Distinct Mouse Testicular Epithelial Cell Lines" (1980) Biology of Reproduction, vol. 23, 243-252.
Mather, Jennie P. et al. "Culture of Testicular Cells in Hormone-Supplemented Serum-Free Medium"(1982) Annuals New York Academy Sciences, vol. 383, 44-68.
Morimoto, Koichi et al., "Single-step purification of F(ab?)2 fragments of mouse monoclonal antibodies (immunoglobulins G1) by hydrophobic interaction high performance liquid chromatography using TSKgel Phenyl-5PW" (1992) Journel of Biochemical and Biophysical Methods, vol. 24, 107-117.
Morrison, Sherie L. et al., "Chimeric human antibody molecules: Mouse antigen-binding domains with human constant region domains" (1984) Proc. Natl. Acad. Sci. USA, vol. 81, 6851-6855.
Mufarrege, Eduardo F. et al. "De-immunized and Functional Therapeutic (DeFT) versions of a long lasting recombinant alpha interferon for antiviral therapy" (2017) Clinical Immunology, vol. 176, 31-41.
Myers, Eugene W. et al. "Optimal alignments in linear space" (1988) CABIOS, vol. 4, No. 1, 11-17.
Pearson, William R., et al. "Improved tools for biological sequence comparison" (1988) Proc Natl Acad Sci USA, vol. 85, 2444-2448.
Pluckthun, A. "Chapter 11, Antibodies from *Escherichia coli*" (1994) In the Pharmacology of Monoclonal Antibodies, vol. 113, 269-315.
Reyes, Gregory R., et al. "Expression of human ?-interferon cDNA under the control of a thymidine kinase promoter from herpes simplex virus" (1982) Nature, vol. 297, 598-601.
Sojar, Hakimuddin T. et al. "A chemical method for the deglycosylation of proteins", (1987) Archives of Biochemstry and Biophysics, vol. 259, No. 1, 52-57.
Stewart, Ross, et al. "The role of Fc gamma receptors in the activity of immunomodulatory antibodies for cancer" (2014) Journal for ImmunoTherapy of Cancer, vol. 2, Issue 1/29, 1-10.
Stinchcomb, D. T. et al., "Isolation and characterisation of a yeast chromosomal replicator" (1979) Nature, vol. 282, 39-43.
Thotakura, Nageswara R. et al. "Enzymatic Deglycosylation of Glycoproteins" (1987) Methods in Enzymology, vol. 138, 350-359.
Torelli, Alberto et al. "Advance and Adam: two algorithms for the analysis of global similarity between homologous informational sequences" (1994) Compu Appl Biosci., vol. 10, No. 1, 3-5.
Urlaub, Gail, et al. "Isolation of Chinese hamster cell mutants deficient in dihydrofolate reductase activity" (1980) Proc Natl Acad Sci USA, vol. 77, 4216-4220.
Van Den Berg, Johan A. et al. "Kluyveromyces as a Host for Heterologous Gene Expression: Expression and Secretion of Prochymosin" (1990) Biotechnology, vol. 8(2), 135-139.
Van Walle, Ivo et al. "Immunogenicity screening in protein drug development" (2007) Expert Opinion on Biological Therapy, vol. 7(3), 405-418.
Wang, Xinhua, et al. "IgG Fc engineering to modulate antibody effector functions"(2018) Protein Cell, vol. 9(1), 63-73.
Yaniv, Moshe "Enhancing elements for activation of eukaryotic promoters" (1987) Nature, vol. 297, 17-18.
Zapata, G. et al., "Engineering linear F(ab')2 fragments for efficient production in *Escherichia coli* and enhanced antiproliferative activity" (1995) Protein Eng., vol. 8(10), 1057-1062.

\* cited by examiner

SEQUENCE LISTING

<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1

<400> SEQUENCE: 1

Gly Phe Thr Phe Ser Ser Tyr Ala Met Ser
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

```
<400> SEQUENCE: 2

Ser Ile Ser Arg Thr Gly Tyr Thr Tyr Tyr Ala Glu Ser Val Lys Gly
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 3

Val Gly Thr Ala Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 4

Arg Ala Ser Gln Ser Ile Ser Ser Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 6

Gln Gln Ser Tyr Ser Thr Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: HCDR1 - Kabat

<400> SEQUENCE: 7

Ser Tyr Ala Met Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1 - Chothia

<400> SEQUENCE: 8

Gly Phe Thr Phe Ser Ser Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2 - Chothia

<400> SEQUENCE: 9

Ser Arg Thr Gly Tyr
1               5

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 1

<400> SEQUENCE: 10

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Ala Glu Ser Val Lys
    50                  55                  60

Gly Arg Phe Thr Ile Ser Arg Asp Glu Ser Lys Gln Thr Leu Tyr Leu
65                  70                  75                  80

Gln Met Gln Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 11
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL - variant a

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 2

<400> SEQUENCE: 12

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Ala Glu Ser Val Lys
50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 3
```

<400> SEQUENCE: 13

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
50                  55                  60

Gly Arg Phe Thr Ile Ser Arg Asp Asp Ser Lys Gln Thr Leu Tyr Leu
65                  70                  75                  80

Gln Met Asn Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH- variant 4

<400> SEQUENCE: 14

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
50                  55                  60

Gly Arg Phe Thr Ile Ser Arg Asp Asp Ser Lys Asn Thr Leu Tyr Leu
65                  70                  75                  80

Gln Met Gln Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH- variant 5

<400> SEQUENCE: 15

Glu Val Gln Leu Leu Glu Ser Gly Gly Gly Leu Val Lys Pro Gly Gly
1               5                   10                  15

-continued

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
    50                  55                  60

Gly Arg Phe Thr Ile Ser Arg Asp Glu Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH- variant 6

<400> SEQUENCE: 16

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
    50                  55                  60

Gly Arg Phe Thr Ile Ser Arg Asp Asp Ser Lys Gln Thr Leu Tyr Leu
65                  70                  75                  80

Gln Met Gln Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH- variant 7

<400> SEQUENCE: 17

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ser Ile Ser Arg Thr Gly Tyr Thr Tyr Tyr Ala Glu Ser Val Lys
            50                  55                  60

Gly Arg Phe Thr Ile Ser Arg Asp Glu Ser Lys Asn Thr Leu Tyr Leu
 65                  70                  75                  80

Gln Met Gln Ser Leu Lys Thr Glu Asp Thr Ala Val Tyr Tyr Cys Ala
                 85                  90                  95

Arg Val Gly Thr Ala Phe Asp Tyr Trp Gly Gln Gly Thr Leu Val Thr
                100                 105                 110

Val Ser Ser
        115

<210> SEQ ID NO 18
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain - Clone I

<400> SEQUENCE: 18

Glu Val Gln Leu Leu Glu Ser Gly Gly Gly Leu Val Lys Pro Gly Gly
 1               5                   10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ser Ile Ser Arg Thr Gly Tyr Thr Tyr Tyr Ala Glu Ser Val Lys
            50                  55                  60

Gly Arg Phe Thr Ile Ser Arg Asp Glu Ser Lys Gln Thr Leu Tyr Leu
 65                  70                  75                  80

Gln Met Gln Ser Leu Lys Thr Glu Asp Thr Ala Val Tyr Tyr Cys Ala
                 85                  90                  95

Arg Val Gly Thr Ala Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light Chain - Clone I

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain - Clone II

<400> SEQUENCE: 20

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Ala Glu Ser Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 21
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain - Clone III

<400> SEQUENCE: 21

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
    50                  55                  60

Gly Arg Phe Thr Ile Ser Arg Asp Asp Ser Lys Gln Thr Leu Tyr Leu
65                  70                  75                  80

Gln Met Asn Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 22
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain- Clone IV

<400> SEQUENCE: 22

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Tyr Ala Glu Ser Val Lys
    50                  55                  60

Gly Arg Phe Thr Ile Ser Arg Asp Asp Ser Lys Asn Thr Leu Tyr Leu
65                  70                  75                  80

Gln Met Gln Ser Leu Lys Thr Glu Asp Thr Ala Val Tyr Tyr Cys Ala
            85                  90                  95

Arg Val Gly Thr Ala Phe Asp Tyr Trp Gly Gln Gly Thr Leu Val Thr
        100                 105                 110

```
Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 23
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain- Clone V

<400> SEQUENCE: 23

Glu Val Gln Leu Leu Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Ser Arg Thr Gly Tyr Thr Tyr Tyr Ala Glu Ser Val Lys
 50                  55                  60

Gly Arg Phe Thr Ile Ser Arg Asp Glu Ser Lys Asn Thr Leu Tyr Leu
 65                  70                  75                  80

Gln Met Asn Ser Leu Lys Thr Glu Asp Thr Ala Val Tyr Tyr Cys Ala
                 85                  90                  95

Arg Val Gly Thr Ala Phe Asp Tyr Trp Gly Gln Gly Thr Leu Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430
```

His Tyr Thr Gln Lys Ser Leu Ser Leu Ser Pro Gly
            435                 440

<210> SEQ ID NO 24
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain- Clone VI

<400> SEQUENCE: 24

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Arg Thr Gly Tyr Thr Tyr Ala Glu Ser Val Lys
    50                  55                  60

Gly Arg Phe Thr Ile Ser Arg Asp Asp Ser Lys Gln Thr Leu Tyr Leu
65                  70                  75                  80

Gln Met Gln Ser Leu Lys Thr Glu Asp Thr Ala Val Tyr Tyr Cys Ala
                85                  90                  95

Arg Val Gly Thr Ala Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 25
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain- Clone VII

<400> SEQUENCE: 25

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Ser Arg Thr Gly Tyr Thr Tyr Tyr Ala Glu Ser Val Lys
50                  55                  60

Gly Arg Phe Thr Ile Ser Arg Asp Glu Ser Lys Asn Thr Leu Tyr Leu
65                  70                  75                  80

Gln Met Gln Ser Leu Lys Thr Glu Asp Thr Ala Val Tyr Tyr Cys Ala
            85                  90                  95

Arg Val Gly Thr Ala Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
            210                 215                 220

Pro Pro Cys Pro Ala Pro Glu Ala Ala Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 26
<211> LENGTH: 923
<212> TYPE: PRT
<213> ORGANISM: Homo sapiens
<220> FEATURE:
<223> OTHER INFORMATION: Human Nrp1A

<400> SEQUENCE: 26

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160
```

```
Pro Gly Phe Pro Glu Lys Tyr Pro Asn Ser Leu Glu Cys Thr Tyr Ile
            165                 170                 175
Val Phe Ala Pro Lys Met Ser Glu Ile Ile Leu Glu Phe Glu Ser Phe
            180                 185                 190
Asp Leu Glu Pro Asp Ser Asn Pro Pro Gly Met Phe Cys Arg Tyr
            195                 200                 205
Asp Arg Leu Glu Ile Trp Asp Gly Phe Pro Asp Val Gly Pro His Ile
            210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
                260                 265                 270
Phe Lys Cys Met Glu Ala Leu Gly Met Glu Ser Gly Glu Ile His Ser
                275                 280                 285
Asp Gln Ile Thr Ala Ser Ser Gln Tyr Ser Thr Asn Trp Ser Ala Glu
                290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                    325                 330                 335
Thr Ala Val Gly Thr Gln Gly Ala Ile Ser Lys Glu Thr Lys Lys Lys
                340                 345                 350
Tyr Tyr Val Lys Thr Tyr Lys Ile Asp Val Ser Ser Asn Gly Glu Asp
                355                 360                 365
Trp Ile Thr Ile Lys Glu Gly Asn Lys Pro Val Leu Phe Gln Gly Asn
            370                 375                 380
Thr Asn Pro Thr Asp Val Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
            435                 440                 445
Ser Ser Asn Gln Gly Asp Arg Asn Trp Met Pro Glu Asn Ile Arg Leu
        450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
                500                 505                 510
Arg Lys Phe Lys Ile Gly Tyr Ser Asn Asn Gly Ser Asp Trp Lys Met
            515                 520                 525
Ile Met Asp Asp Ser Lys Arg Lys Ala Lys Ser Phe Glu Gly Asn Asn
        530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
```

```
                580             585             590
Thr Thr Pro Asn Gly Asn Leu Val Asp Glu Cys Asp Asp Gln Ala
            595                 600             605
Asn Cys His Ser Gly Thr Gly Asp Asp Phe Gln Leu Thr Gly Gly Thr
    610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
            660                 665                 670
Trp Ser Val Leu Thr Ser Lys Thr Gly Pro Ile Gln Asp His Thr Gly
        675                 680                 685
Asp Gly Asn Phe Ile Tyr Ser Gln Ala Asp Glu Asn Gln Lys Gly Lys
    690                 695                 700
Val Ala Arg Leu Val Ser Pro Val Val Tyr Ser Gln Asn Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
            740                 745                 750
Trp Met Ala Ile Gly His Gln Gly Asp His Trp Lys Glu Gly Arg Val
        755                 760                 765
Leu Leu His Lys Ser Leu Lys Leu Tyr Gln Val Ile Phe Glu Gly Glu
    770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
                805                 810                 815
Lys Lys Asn Pro Glu Ile Lys Ile Asp Glu Thr Gly Ser Thr Pro Gly
            820                 825                 830
Tyr Glu Gly Glu Gly Glu Gly Asp Lys Asn Ile Ser Arg Lys Pro Gly
        835                 840                 845
Asn Val Leu Lys Thr Leu Asp Pro Ile Leu Ile Thr Ile Ile Ala Met
    850                 855                 860
Ser Ala Leu Gly Val Leu Leu Gly Ala Val Cys Gly Val Val Leu Tyr
865                 870                 875                 880
Cys Ala Cys Trp His Asn Gly Met Ser Glu Arg Asn Leu Ser Ala Leu
                885                 890                 895
Glu Asn Tyr Asn Phe Glu Leu Val Asp Gly Val Lys Leu Lys Lys Asp
            900                 905                 910
Lys Leu Asn Thr Gln Ser Thr Tyr Ser Glu Ala
        915                 920

<210> SEQ ID NO 27
<211> LENGTH: 10
<212> TYPE: PRT
<213> ORGANISM: Homo sapiens
<220> FEATURE:
<223> OTHER INFORMATION: Epitope

<400> SEQUENCE: 27

Met Ile Asn Phe Asn Pro His Phe Asp Leu
1               5                   10
```

```
<210> SEQ ID NO 28
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW64.3- HC

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Glu
            20                  25                  30

Pro Ile Ser Trp Val Arg Gln Ala Pro Gly Lys Gly Leu Glu Trp Val
        35                  40                  45

Ser Ser Ile Thr Gly Lys Asn Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly Lys Lys Val Tyr Gly Met Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 29
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW64.3-LC

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Ser Val Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 119
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: YW64.3-VH

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Glu
            20                  25                  30

Pro Ile Ser Trp Val Arg Gln Ala Pro Gly Lys Gly Leu Glu Trp Val
        35                  40                  45

Ser Ser Ile Thr Gly Lys Asn Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly Lys Lys Val Tyr Gly Met Asp Val Trp Gly Gln Gly
            100                 105                 110

Thr Leu Val Thr Val Ser Ser
            115

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW64.3-VL

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Ser Val Pro Ile
                85                  90                  95

Thr Phe Gly Gln Gly Thr Lys Val Glu Ile Lys Arg
            100                 105

<210> SEQ ID NO 32
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW107.4.87- HC

<400> SEQUENCE: 32
```

-continued

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Gln Ile Ser Pro Ala Gly Gly Tyr Thr Asn Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Glu Leu Pro Tyr Tyr Arg Met Ser Lys Val Met Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
```

```
                    420                 425                 430
Val Met His Glu Ala Leu His Asn His Tyr Thr Gln Lys Ser Leu Ser
        435                 440                 445

Leu Ser Pro Gly Lys
    450

<210> SEQ ID NO 33
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW107.4.87- LC

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW107.4.87- VH

<400> SEQUENCE: 34

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ser Phe Ser Tyr Ala
            20                  25                  30

Met Ser Trp Val Arg Gln Ala Pro Gly Lys Gly Leu Glu Trp Val Ser
        35                  40                  45

Gln Ile Ser Pro Ala Gly Gly Tyr Thr Asn Tyr Ala Asp Ser Val Lys
        50                  55                  60

Gly Arg Phe Thr Ile Ser Ala Asp Thr Ser Lys Asn Thr Ala Tyr Leu
65                      70                  75                  80

Gln Met Asn Ser Leu Arg Ala Glu Asp Thr Ala Val Tyr Tyr Cys Ala
                85                  90                  95

Arg Glu Leu Pro Tyr Tyr Arg Met Ser Lys Val Met Asp Val Trp Gly
                100                 105                 110

Gln Gly Thr Leu Val Thr Val Ser Ser
            115                 120

<210> SEQ ID NO 35
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: YW107.4.87- VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg
                100                 105
```

US 11,661,458 B2

ANTI-NRP1A ANTIBODIES AND THEIR USES FOR TREATING EYE OR OCULAR DISEASES

SEQUENCE LISTING

The instant application contains a Sequence Listing which has been submitted electronically in ASCII format and is hereby incorporated by reference in its entirety. Said ASCII copy, created on Sep. 15, 2020, is named 01-3397-US-1_SLFINAL.txt and is 66,385 bytes in size.

FIELD OF THE INVENTION

This invention generally relates to antibodies and fragments thereof that target Neuropilin 1 (Nrp1), more precisely the A-domain of Nrp1 (Nrp1A). More specifically, anti-Nrp1A antibodies and methods of use for the treatment of various diseases or disorders are disclosed. Pharmaceutical compositions comprising the anti-Nrp1A antibody are also disclosed.

BACKGROUND OF THE INVENTION

Diabetic retinopathy is one of the most debilitating complications of diabetes mellitus. Despite major advances in understanding the pathogenesis of this disease and the efficacy of current therapies, diabetic retinopathy remains the leading cause of new-onset blindness among working-age people.

Diabetic retinopathy is characterized by a progression of abnormalities occuring on the vascular, glial and neuronal level. One of the vascular complications is a loss of small capillary vessels resulting in retinal ischemia. Ischemic retinopathies are characterized by loss or dysfunction of the retinal vasculature, which results in a reduction of blood flow and hypoxia. The capillary dropout often manifests around the foveal avascular zone (FAZ) thereby extending its size, a condition called diabetic macular ischemia (DMI). Ischemia of the retina leads to up-regulation of pro-angiogenic growth factors and vasorepulsion factors at the same time, leading to a misdirection of angiogenesis. Revascularization of the ischemic retina does not occur, while there is robust pathologic neovascularization into the vitreous, a region of the eye normally devoid of blood vessels. The growth of these abnormal new vessels in proliferative retinopathies creates most of the threat to vision since they can leak, lead to hemorrhage or lead to scarring that may end in retinal detachment. Current treatments for proliferative retinopathies seek to destroy the existing pathological vessels but do not address the underlying ischemia that drives their growth. Currently, standard treatment for proliferative retinopathy involves destruction of a portion of the retina with a laser in an attempt to stop new vessel growth and preserve central vision. These treatments are however to some extent inefficient. While some patients may maintain a stable vision for many years, a high percentage of patients suffering from retinopathy eventually suffers from total visual loss.

Retinopathies may also be characterized by an increased retinal vascular leakage resulting in macular edema. Currently, patients suffering from diabetic macular edema are treated with compounds targeting vascular endothelial growth factor A (VEGF-A), a growth factor that is driving both angiogenesis and vascular permeability. This therapeutic strategy may prove insufficient for treating patients who suffers from both macular ischemia and macular edema.

There is thus still a need for a therapeutic approach to treat patients who could benefit from the pro-angiogenic properties of VEGF-A, in particular in patients suffering from both macular ischemia and macular edema. Consequently, there is still an unfulfilled need for new therapeutic approaches for efficiently treating eye or retinal diseases.

SUMMARY OF THE INVENTION

Neuropilins (NRPs) are transmembrane glycoprotein receptors that play an important role in the development of the neuronal and vascular systems as receptors for members of the class-3 semaphorin family (SEMAs) of axonal guidance factors and members of the vascular endothelial growth factor (VEGF) family of angiogenesis factors. Two neuropilin proteins, neuropilin-1 (Nrp-1) and neuropilin-2 (Nrp-2) have been identified. Their extracellular region contains three domains: two CUB homology domains (A-domain of Nrp1, also referred herein as "Nrp1A") as Sema3 ligand-binding domain, two coagulation factor V/VIII homology domains (B-domain of Nrp1, also referred herein as "Nrp1B") as VEGF binding domain, and a MAM domain (c) involved in Nrp-1 dimerization. Nrp-1 can bind VEGF-A165, VEGF-B, VEGF-E, PlGF, Sema3A, Sema3B and Sema3C, whereas Nrp2 binds VEGF-A165, VEGF-A145, VEGF-C, VEGF-D, SEMA3B, Sema3C, Sema3F and Sema3G. The binding site for VEGF ligands has been localized on the B-domain of Nrp1 whereas the binding of semaphorins has been localized on the A-domain of Nrp1.

The sequence of human Nrp1 is available online, the Nrp1 isoform A precursor is depicted in SEQ ID NO: 26 and is available under the Reference protein sequence NP_003864. Nrp1 has been studied in tumor angiogenesis and metastasis for years, but its effects on retinal revascularization and neovascularization are not fully understood. The inventors have shown here that targeting Nrp1, especially the A-domain of Nrp1, is a highly effective strategy for treating eye and retinal diseases.

In a first aspect, the present invention provides an anti-Nrp1A antibody or an antigen-binding fragment thereof comprising:
  a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
  a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In one embodiment, the present invention provides an anti-Nrp1A antibody or an antigen-binding fragment thereof comprising:
  a heavy chain variable region comprising an amino acid sequence at least 80%, at least 90%, at least 95%, at least 98%, or at least 99% identical to the amino acid sequence of SEQ ID NO: 10, SEQ ID NO: 12, SEQ ID NO: 13, SEQ ID NO: 14, SEQ ID NO: 15, SEQ ID NO: 16 or SEQ ID NO: 17; and
  a light chain variable region comprising an amino acid sequence at least 80%, at least 90%, at least 95%, at least 98%, or at least 99% identical to the amino acid sequence of SEQ ID NO: 11.

In one embodiment, the present invention provides an anti-Nrp1A antibody or an antigen-binding fragment thereof comprising:
  a heavy chain variable region comprising an amino acid sequence at least 80%, at least 90%, at least 95%, at least 98%, or at least 99% identical to the amino acid sequence of SEQ ID NO: 10, SEQ ID NO: 12, SEQ ID NO: 13, SEQ ID NO: 14, SEQ ID NO: 15, SEQ ID NO: 16 or SEQ ID NO: 17; and a light chain variable region comprising an amino acid sequence at least 80%, at least 90%, at least 95%, at least 98%, or at least 99% identical to the amino acid sequence of SEQ ID NO: 11;

wherein:

the heavy chain variable region comprises the amino acid sequence of SEQ ID NO: 1 (H-CDR1), the amino acid sequence of SEQ ID NO: 2 (H-CDR2), and the amino acid sequence of SEQ ID NO: 3 (H-CDR3); and the light chain variable region comprising the amino acid sequence of SEQ ID NO: 4 (L-CDR1), the amino acid sequence of SEQ ID NO: 5 (L-CDR2), and the amino acid sequence of SEQ ID NO: 6 (L-CDR3).

In yet another embodiment, the present invention provides an anti-Nrp1A antibody or an antigen-binding fragment thereof comprising:

a heavy chain variable region comprising the amino acid sequences of SEQ ID NO: 10, SEQ ID NO: 12, SEQ ID NO: 13, SEQ ID NO: 14, SEQ ID NO: 15, SEQ ID NO: 16 or SEQ ID NO: 17; and a light chain variable region comprising the amino acid sequence of SEQ ID NO: 11.

In another embodiment, the present invention provides an anti-Nrp1A antibody or an antigen-binding fragment thereof comprising:

a. a variable heavy chain and a variable light chain comprising the amino acid sequences of SEQ ID NO: 10 and SEQ ID NO: 11, respectively;
b. a variable heavy chain and a variable light chain comprising the amino acid sequences of SEQ ID NO: 12 and SEQ ID NO: 11, respectively;
c. a variable heavy chain and a variable light chain comprising the amino acid sequences of SEQ ID NO: 13 and SEQ ID NO: 11, respectively;
d. a variable heavy chain and a variable light chain comprising the amino acid sequences of SEQ ID NO: 14 and SEQ ID NO: 11, respectively;
e. a variable heavy chain and a variable light chain comprising the amino acid sequences of SEQ ID NO: 15 and SEQ ID NO: 11, respectively;
f. a variable heavy chain and a variable light chain comprising the amino acid sequences of SEQ ID NO: 16 and SEQ ID NO: 11, respectively; or
g. a variable heavy chain and a variable light chain comprising the amino acid sequences of SEQ ID NO: 17 and SEQ ID NO: 11, respectively.

In yet another embodiment, the present invention provides an anti-Nrp1A antibody or an antigen-binding fragment thereof comprising:

a heavy chain comprising, preferably consisting of, the amino acid sequence of SEQ ID NO: 18, SEQ ID NO: 20, SEQ ID NO: 21, SEQ ID NO: 22, SEQ ID NO: 23, SEQ ID NO: 24 or SEQ ID NO: 25; and a light chain comprising, preferably consisting of, the amino acid sequence of SEQ ID NO: 19.

In a particular embodiment, the invention relates to an anti-Nrp1A antibody or an antigen-binding fragment thereof comprising:

a. a heavy chain comprising the amino acid sequence of SEQ ID NO: 18 and a light chain comprising the amino acid sequence of SEQ ID NO: 19;
b. a heavy chain comprising the amino acid sequence of SEQ ID NO: 20 and a light chain comprising the amino acid sequence of SEQ ID NO: 19;
c. a heavy chain comprising the amino acid sequence of SEQ ID NO: 21 and a light chain comprising the amino acid sequence of SEQ ID NO: 19;
d. a heavy chain comprising the amino acid sequence of SEQ ID NO: 22 and a light chain comprising the amino acid sequence of SEQ ID NO: 19;
e. a heavy chain comprising the amino acid sequence of SEQ ID NO: 23 and a light chain comprising the amino acid sequence of SEQ ID NO: 19;
f. a heavy chain comprising the amino acid sequence of SEQ ID NO: 24 and a light chain comprising the amino acid sequence of SEQ ID NO: 19; or
g. a heavy chain comprising the amino acid sequence of SEQ ID NO: 25 and a light chain comprising the amino acid sequence of SEQ ID NO: 19.

In a particular preferred embodiment, the anti-Nrp1A antibody is a humanized anti-Nrp1A antibody.

In a second aspect, the present invention provides an anti-Nrp1A antibody or an antigen-binding fragment thereof that binds to at least one amino acid residue within amino acid regions 68-77 of the human Nrp1 as depicted in SEQ ID NO: 26.

In one embodiment, the present invention provides an anti-Nrp1A antibody or an antigen-binding fragment thereof that binds to at least one amino acid residue within amino acid regions as set forth in SEQ ID NO: 26. In a preferred embodiment, the present invention provides an anti-Nrp1A antibody or an antigen-binding fragment thereof that binds the amino acid regions as set forth in SEQ ID NO: 27.

In a third aspect, the present invention provides an anti-Nrp1A antibody or an antigen-binding fragment thereof for use as a medicament.

In one embodiment, the present invention provides an anti-Nrp1A or an antigen-binding fragment for inhibiting the vasorepulsive effect of Sema3A, and/or for improving revascularisation of the retina. In a further embodiment, the present invention provides an anti-Nrp1A or an antigen-binding fragment for inhibiting the permeability of the blood retinal barrier (BRB) induced by Sema3A and for inhibiting the permeability of the blood retinal barrier induced by VEGF, preferably VEGF-A.

In yet a further embodiment, the present invention provides an anti-Nrp1A or an antigen-binding fragment for:

redirecting angiogenesis towards ischemic regions, in order to improve revascularisation of the retina;
preventing pathological neovascularization of the vitreous region;
preventing the blood retinal barrier breakdown induced by Sema3A; and
preventing the blood retinal barrier breakdown induced by VEGF-A.

In one embodiment, the present invention provides an anti-Nrp1A antibody or an antigen-binding fragment thereof for use in the treatment or prevention of a retinal or eye disease.

In another embodiment, the present invention relates to a method for treating one or more retinal or eye diseases, comprising administering a pharmaceutically effective amount of an antibody or an antigen-binding fragment according to a patient in need thereof.

In a fourth aspect, the present invention provides an anti-Nrp1A antibody or an antigen-binding fragment thereof for use in the treatment or prevention of a disease selected from the group consisting of retinopathy, proliferative retinopathy (PR) such as retinopathy of prematurity, ischemic retinopathy, diabetic retinopathy (DR) including proliferative diabetic retinopathy (PDR) and non-proliferative diabetic retinopathy, diabetic macular edema (DME), diabetic macular ischemia (DMI), age-related macular degeneration, retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease.

In another embodiment, the present invention provides an anti-Nrp1A antibody or an antigen-binding fragment thereof for use in the treatment or prevention of a disease selected from the group consisting of diabetic retinopathy including proliferative diabetic retinopathy and non-proliferative diabetic retinopathy, ischemic retinopathy, diabetic macular edema, diabetic macular ischemia, age-related macular edema, retinal neovascularization, glaucoma and choroidal neovascularization. Preferably, said disease is diabetic macular edema and/or diabetic macular ischemia.

In a preferred embodiment, the present invention provides an anti-Nrp1A antibody or an antigen-binding fragment thereof for use in the treatment of diabetic macular ischemia, by promoting vascular regeneration within the ischemic retina (revascularization) and reducing pathological neovascularization of the vitreous region of the eye. In one embodiment, the antibody according to the invention does not inhibit the angiogenesis induced by VEGF, preferably VEGF-A.

In another preferred embodiment, the present invention provides an anti-Nrp1A antibody or an antigen-binding fragment thereof for use in the treatment of diabetic macular edema, by reducing, preferably preventing, the permeability of blood retinal barrier induced by Sema3A and by reducing, preferably preventing, the permeability of blood retinal barrier induced by VEGF-A.

In a fifth aspect, the present invention provides a pharmaceutical composition comprising an anti-Nrp1A antibody or an antigen-binding fragment thereof and a pharmaceutically acceptable carrier.

In one embodiment, the present invention provides an anti-Nrp1A antibody or an antigen-binding fragment thereof or a pharmaceutical composition comprising an anti-Nrp1A antibody or an antigen-binding fragment thereof, wherein said antibody or an antigen-binding fragment thereof is administered by a parenteral route, intravenous route, intravitreal route or subcutaneous route of administration, preferably by intravitreal route.

In a sixth aspect, the present invention provides an isolated polynucleotide or polynucleotides comprising:
   a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and
   a sequence encoding a light chain as shown in SEQ ID NO: 19 or a light chain variable region as shown in SEQ ID NO: 11.

In one embodiment, the present invention provides an expression vector comprising an isolated polynucleotide or polynucleotides comprising a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and a sequence encoding a light chain as shown in SEQ ID NO: 19 or a light chain variable region as shown in SEQ ID NO: 11.

In one embodiment, the present invention provides a viral vector comprising an isolated polynucleotide or polynucleotides comprising a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and a sequence encoding a light chain as shown in SEQ ID NO: 19 or a light chain variable region as shown in SEQ ID NO: 11.

In one embodiment, the present invention provides a host cell comprising an expression vector or an isolated polynucleotide or polynucleotides comprising a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and a sequence encoding a light chain as shown in SEQ ID NO: 19 or a light chain variable region as shown in SEQ ID NO: 11.

In one embodiment, the present invention provides a method for producing an anti-Nrp1A antibody or an antigen-binding fragment thereof comprising obtaining a host cell comprising an expression vector or an isolated polynucleotide or polynucleotides comprising a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and a sequence encoding a light chain as shown in SEQ ID NO: 19 or a light chain variable region as shown in SEQ ID NO: 11; and cultivating the host cell.

In one embodiment, the method for producing an anti-Nrp1A antibody or an antigen-binding fragment thereof further comprises recovering and purifying the anti-Nrp1A antibody or an antigen-binding fragment thereof.

BRIEF DESCRIPTION OF THE DRAWINGS

FIG. 4 further shows that following this interaction, the antibody of the invention is still capable of binding to hNrp1 even while it is simultaneously bound to hVEGF165. This indicates that the antibody of the invention does not prevent the binding of VEGF and human Nrp1.

DETAILED DESCRIPTION OF THE INVENTION

Definitions

Figure 1A:
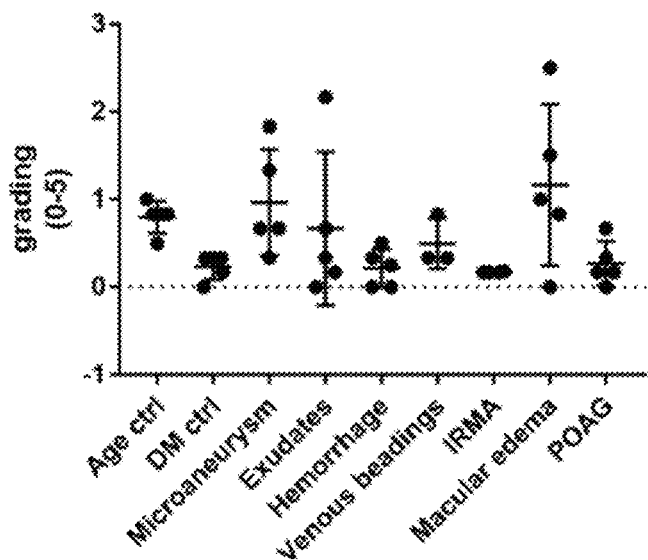
FIGS. 1A and 1B shows the localization of Sema3A in human eyes in prespecified retinal samples from human donors with a history of Diabetic Retinopathy or primary open angle glaucoma (POAG) in comparison to age matched controls (Age ctrl) and subjects with Diabetes, but no ocular pathology (DM ctrl). Sema3A was found in the vasculature wall of retinal blood vessels (FIG. 1A). Additionally, unidentified but distinctive Sema3A fluorescent objects were observed in the retinal ganglion cell layer (FIG. 1B).

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain (CL). The $V_L$ domain associates non-covalently with the $V_H$ domain, whereas the CL domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops ($HVL_S$). CDRs are defined by sequence comparison in Kabat et al., 1991, In: Sequences of Proteins of Immunological Interest, 5th Ed. Public Health Service, National Institutes of Health, Bethesda, Md., whereas $HVL_S$ are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-$H_1$ is positioned at about residues 31-35, CDR-$H_2$ at about residues 50-65, and CDR-$H_3$ at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-Nrp1A antibody", "humanized anti-Nrp1A antibody", and "variant humanized anti-Nrp1A antibody" are used herein in the broadest sense and specifically encompass monoclonal antibodies (including full length monoclonal antibodies), multispecific antibodies (e.g., bispecific antibodies), and antibody fragments such as variable domains and other portions of antibodies that exhibit a desired biological activity, e.g., binding to Nrp1A.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "antigen binding fragment", "anti-Nrp1A antibody fragment", "humanized anti-Nrp1A antibody fragment", "variant humanized anti-Nrp1A antibody fragment" refer to a portion of a full length anti-Nrp1A antibody, in which a variable region or a functional capability is retained, for example, specific Nrp1 epitope binding. Examples of antibody fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or $HVL_S$ of a non-human antibody, inserted between the FRs of a human heavy or light chain variable domain.

The present invention describes specific humanized anti-Nrp1A antibodies which contain CDRs derived from a murine or chimeric antibody inserted between the FRs of human germline sequence heavy and light chain variable domains. It will be understood that certain murine FR residues may be important to the function of the humanized antibodies and therefore certain of the human germline sequence heavy and light chain variable domains residues are modified to be the same as those of the corresponding murine sequence.

As used herein, the expressions "antibody of the invention" and the "anti-Nrp1A antibody of the invention" refer to an antibody directed against Nrp1, preferably the A-domain of Nrp1, or an antigen-binding fragment thereof described herein. Preferably, said antibody of the invention comprises a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In one embodiment, the invention relates to a humanized anti-Nrp1A. Humanized antibodies comprise substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, the CDRs are murine sequences, and the FRs are those of a human immunoglobulin consensus or germline sequence. In another aspect, a humanized anti-Nrp1A antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-Nrp1A antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-Nrp1A antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly IgG1 antibodies characterized by a reduced effector function.

In a preferred embodiment, the anti-Nrp1A antibody of the invention is a humanized antibody formatted as IgG1KO.

The FRs and CDRs, or $HVL_S$, of a humanized anti-Nrp1A antibody do need not to correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to Nrp1. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-Nrp1A antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly, the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

The term "antibody performance" refers to factors/properties that contribute to antibody recognition of antigen or the effectiveness of an antibody in vivo. In a preferred embodiment, it refers to the ability of the antibody to prevent cytoskeletal collapse in retinal cells. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half-life of the antibody.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disease" or "disorder", as used herein, is any condition that would benefit from treatment with a humanized anti-Nrp1A antibody described herein. This includes chronic and acute disorders or diseases including those pathological conditions that predispose the mammal to the disorder in question.

The term "intravitreal injection" has its normal meaning in the art and refers to introduction of an anti-Nrp1A antibody or an antigen-binding fragment thereof into the vitreous of a patient.

The term "subcutaneous administration" refers to introduction of an anti-Nrp1A antibody or an antigen-binding fragment thereof under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an anti-Nrp1A antibody or an antigen-binding fragment thereof that relieves or ameliorates one or more of the symptoms of the disorder being treated. In doing so it is that amount that has a beneficial patient outcome. Efficacy can be measured in conventional ways, depending on the condition to be treated. For example, in eye/retinal diseases or disorders characterized by cells expressing Nrp1A, efficacy can be measured by determining the response rates, e.g. restoration of vision or by assessing the time of delay until disease progression.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-Nrp1A antibody or an antigen-binding fragment thereof prior to or following the onset of a symptom of a disease or disorder thereby preventing or removing one or more signs of the disease or disorder. As another example, the term includes the administration of an anti-Nrp1A antibody or an antigen-binding fragment thereof after clinical manifestation of the disease to combat the symptoms of the disease. Further, administration of an anti-Nrp1A antibody or an antigen-binding fragment thereof after onset and after clinical symptoms have developed where administration affects clinical parameters of the disease or disorder, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-Nrp1A antibody composition or an antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibody of the Invention

In a first aspect, the invention relates to an anti-Nrp1A antibody or an antigen binding fragment thereof. Preferably, said antibody is a humanized anti-Nrp1A antibody, more preferably a humanized monoclonal anti-Nrp1A antibody.

In an initial characterization, a library of antibodies targeting Nrp1A variants was generated by placing the CDRs of murine antibodies or of human antibodies derived from a phage library into FRs of the human consensus heavy and light chain variable domains and furthermore by engineering the FRs with different alterations.

This resulted in a humanized antibody directed against Nrp1A with enhanced properties as disclosed herein. The sequences of the antibodies of the invention are shown in Table 1 below.

TABLE 1

| Name | Amino acid sequence | SEQ ID NO |
|---|---|---|
| HCDR1 | GFTFSSYAMS | 1 |
| HCDR2 | SISRTGYTYYAESVKG | 2 |
| HCDR3 | VGTAFDY | 3 |
| LCDR1 | RASQSISSYLN | 4 |
| LCDR2 | AASSLQS | 5 |
| LCDR3 | QQSYSTPLT | 6 |
| VH-variant 1 | EVQLLESGGGLVKPGGSLRLSCAASGFTFSSYAMSWVRQAPGKGLEWVSSISRTGYTYYAESVKGRFTISRDESKQTLYLQMQSLKTEDTAVYYCARVGTAFDYWGQGTLVTVSS | 10 |
| VL-variant a | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK | 11 |
| VH-variant 2 | EVQLLESGGGLVKPGGSLRLSCAASGFTFSSYAMSWVRQAPGKGLEWVSSISRTGYTYYAESVKGRFTISRDDSKNTLYLQMNSLKTEDTAVYYCARVGTAFDYWGQGTLVTVSS | 12 |

TABLE 1-continued

| Name | Amino acid sequence | SEQ ID NO |
|---|---|---|
| VH-variant 3 | EVQLLESGGGLVKPGGSLRLSCAASGFTFSSYAMSWVRQAPGKGLEWVSSISRT GYTYYAESVKGRFTISRDDSKQTLYLQMNSLKTEDTAVYYCARVGTAFDYWGQG TLVTVSS | 13 |
| VH-variant 4 | EVQLLESGGGLVKPGGSLRLSCAASGFTFSSYAMSWVRQAPGKGLEWVSSISRT GYTYYAESVKGRFTISRDDSKNTLYLQMQSLKTEDTAVYYCARVGTAFDYWGQG TLVTVSS | 14 |
| VH-variant 5 | EVQLLESGGGLVKPGGSLRLSCAASGFTFSSYAMSWVRQAPGKGLEWVSSISRT GYTYYAESVKGRFTISRDESKNTLYLQMNSLKTEDTAVYYCARVGTAFDYWGQG TLVTVSS | 15 |
| VH-variant 6 | EVQLLESGGGLVKPGGSLRLSCAASGFTFSSYAMSWVRQAPGKGLEWVSSISRT GYTYYAESVKGRFTISRDDSKQTLYLQMSLKTEDTAVYYCARVGTAFDYWGQG TLVTVSS | 16 |
| VH-variant 7 | EVQLLESGGGLVKPGGSLRLSCAASGFTFSSYAMSWVRQAPGKGLEWVSSISRT GYTYYAESVKGRFTISRDESKNTLYLQMSLKTEDTAVYYCARVGTAFDYWGQG TLVTVSS | 17 |
| Heavy Chain-Clone I | EVQLLESGGGLVKPGGSLRLSCAASGFTFSSYAMSWVRQAPGKGLEWVSSISRT GYTYYAESVKGRFTISRDESKQTLYLQMSLKTEDTAVYYCARVGTAFDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPK SCDKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHN HYTQKSLSLSPG | 18 |
| Light Chain-Clone I | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone II | EVQLLESGGGLVKPGGSLRLSCAASGFTFSSYAMSWVRQAPGKGLEWVSSISRT GYTYYAESVKGRFTISRDDSKNTLYLQMQSLKTEDTAVYYCARVGTAFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPEAAGGPSVFLFPPKPKDTLMISRTPEVTCVVVDVSHEDPEVKF NWYVDGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 20 |
| Light Chain-Clone III | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone III | EVQLLESGGGLVKPGGSLRLSCAASGFTFSSYAMSWVRQAPGKGLEWVSSISRT GYTYYAESVKGRFTISRDDSKQTLYLQMNSLKTEDTAVYYCARVGTAFDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPKS CDKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 21 |
| Light Chain-Clone IV | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone IV | EVQLLESGGGLVKPGGSLRLSCAASGFTFSSYAMSWVRQAPGKGLEWVSSISRT GYTYYAESVKGRFTISRDDSKNTLYLQMSLKTEDTAVYYCARVGTAFDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPKS CDKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 22 |

TABLE 1-continued

| Name | Amino acid sequence | SEQ ID NO |
|---|---|---|
| Light Chain-Clone V | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone V | EVQLLESGGGLVKPGGSLRLSCAASGFTFSSYAMSWVRQAPGKGLEWVSSISRT GYTYYAESVKGRFTISRDESKNTLYLQMNSLKTEDTAVYYCARVGTAFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKS CDKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 23 |
| Light Chain-Clone VI | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone VI | EVQLLESGGGLVKPGGSLRLSCAASGFTFSSYAMSWVRQAPGKGLEWVSSISRT GYTYYAESVKGRFTISRDDSKQTLYLQMQSLKTEDTAVYYCARVGTAFDYWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPKS CDKTHTCPPCPAPEAAGGPSVFLFPPKPKDTLMISRTPEVTCVVVDVSHEDPEVK FNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 24 |
| Light Chain-Clone VII | DIQMTQSPSSLSASVGDRVTITCRASQSISSYLNWYQQKPGKAPKLLIYAASSLQS GVPSRFSGSGSGTDFTLTISSLQPEDFATYYCQQSYSTPLTFGGGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC | 19 |
| Heavy Chain-Clone VII | EVQLLESGGGLVKPGGSLRLSCAASGFTFSSYAMSWVRQAPGKGLEWVSSISRT GYTYYAESVKGRFTISRDESKNTLYLQMQSLKTEDTAVYYCARVGTAFDYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPEAAGGPSVFLFPPKPKDTLMISRTPEVTCVVVDVSHEDPEVKF NWYVDGVEVHNAKTKPREEQYNSTYRVVSVLTVLHQDWLNGKEYKCKVSNKAL PAPIEKTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALHNHY TQKSLSLSPG | 25 |

In one embodiment, the present invention provides an anti-Nrp1A antibody or an antigen-binding fragment thereof comprising:
a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In another embodiment, the present invention provides an anti-Nrp1A antibody or an antigen-binding fragment thereof comprising:
a heavy chain variable region comprising an amino acid sequence at least 80%, at least 90%, at least 95%, at least 98%, or at least 99% identical to the amino acid sequence of SEQ ID NO: 10, SEQ ID NO: 12, SEQ ID NO: 13; SEQ ID NO: 14, SEQ ID NO: 15, SEQ ID NO: 16, or SEQ ID NO: 17; and
a light chain variable region comprising an amino acid sequence at least 80%, at least 90%, at least 95%, at least 98%, or at least 99% identical to the amino acid sequence of SEQ ID NO: 11.

In yet another embodiment, the present invention provides an anti-Nrp1A antibody or an antigen-binding fragment thereof comprising:
a heavy chain variable region comprising the amino acid sequences of SEQ ID NO: 10, SEQ ID NO: 12, SEQ ID NO: 13; SEQ ID NO: 14, SEQ ID NO: 15, SEQ ID NO: 16, or SEQ ID NO: 17 and
a light chain variable region comprising the amino acid sequence of SEQ ID NO: 11.

In a preferred embodiment, the invention provides an anti-Nrp1A antibody or an antigen-binding fragment thereof comprising:
a. a variable heavy chain and a variable light chain comprising the amino acid sequences of SEQ ID NO: 10 and SEQ ID NO: 11, respectively;
b. a variable heavy chain and a variable light chain comprising the amino acid sequences of SEQ ID NO: 12 and SEQ ID NO: 11, respectively;
c. a variable heavy chain and a variable light chain comprising the amino acid sequences of SEQ ID NO: 13 and SEQ ID NO: 11, respectively;
d. a variable heavy chain and a variable light chain comprising the amino acid sequences of SEQ ID NO: 14 and SEQ ID NO: 11, respectively;

e. a variable heavy chain and a variable light chain comprising the amino acid sequences of SEQ ID NO: 15 and SEQ ID NO: 11, respectively;
f. a variable heavy chain and a variable light chain comprising the amino acid sequences of SEQ ID NO: 16 and SEQ ID NO: 11, respectively; or
g. a variable heavy chain and a variable light chain comprising the amino acid sequences of SEQ ID NO: 17 and SEQ ID NO: 11, respectively.

In yet another embodiment, the present invention provides an anti-Nrp1A antibody or an antigen-binding fragment thereof comprising:
  a heavy chain comprising, preferably consisting of, the amino acid sequence of SEQ ID NO: 18, SEQ ID NO: 20, SEQ ID NO: 21, SEQ ID NO: 22, SEQ ID NO: 23, SEQ ID NO: 24 or SEQ ID NO: 25; and
  a light chain comprising, preferably consisting of, the amino acid sequence of SEQ ID NO: 19.

In yet another embodiment, the present invention provides an anti-Nrp1A antibody or an antigen-binding fragment thereof comprising:
  a. a heavy chain comprising the amino acid sequence of SEQ ID NO: 18 and a light chain comprising the amino acid sequence of SEQ ID NO: 19, said antibody being referred to as "clone I";
  b. a heavy chain comprising the amino acid sequence of SEQ ID NO: 20 and a light chain comprising the amino acid sequence of SEQ ID NO: 19, said antibody being referred to as "clone II";
  c. a heavy chain comprising the amino acid sequence of SEQ ID NO: 21 and a light chain comprising the amino acid sequence of SEQ ID NO: 19, said antibody being referred to as "clone III";
  d. a heavy chain comprising the amino acid sequence of SEQ ID NO: 22 and a light chain comprising the amino acid sequence of SEQ ID NO: 19, said antibody being referred to as "clone IV";
  e. a heavy chain comprising the amino acid sequence of SEQ ID NO: 23 and a light chain comprising the amino acid sequence of SEQ ID NO: 19, said antibody being referred to as "clone V";
  f. a heavy chain comprising the amino acid sequence of SEQ ID NO: 24 and a light chain comprising the amino acid sequence of SEQ ID NO: 19, said antibody being referred to as "clone VI"; or
  g. a heavy chain comprising the amino acid sequence of SEQ ID NO: 25 and a light chain comprising the amino acid sequence of SEQ ID NO: 19, said antibody being referred to as "clone VII".

IgG1-KO mutants have been made by introducing mutations in the Fc region. Mutations to reduce or inhibit effector function are well known by the skilled person and thoroughly disclosed in prior art, for example in Wang et al, Protein Cell 2018, 9(1):63-73 and Stewart et al. Journal for ImmunoTherapy of Cancer 2014, 2:29. Typically, a non limiting list of mutations introduced in the IgG1 Fc region in order to reduce the effector function of the Fc comprises:
  L234A and L235A;
  L234A, L235A, and N297Q;
  L234A, L235A, and P329G; or
  L234A, L235A, and D265A;
wherein the residues are numbered according to the EU index of Kabat.

In a preferred embodiment, the antibody of the invention comprises the two mutations L234A and L235A in the Fc region to reduce effector function.

The CDR disclosed herein and depicted in SEQ ID NO: 1 to 6 are presented according to the CCG (Chemical Computing Group as illustrated in Almagro et al., Proteins 2011; 79:3050-3066 and Maier et al, Proteins 2014; 82:1599-1610) in Table 2 below.

TABLE 2

| CDR | CCG Seq | CCG Position | SEQ ID NO: |
|---|---|---|---|
| HCDR1 | GFTFSSYAMS | 26-35 | 1 |
| HCDR2 | SISRTGYTYYAESVKG | 50-65 | 2 |
| HCDR3 | VGTAFDY | 98-104 | 3 |
| LCDR1 | RASQSISSYLN | 24-34 | 4 |
| LCDR2 | AASSLQS | 50-56 | 5 |
| LCDR3 | QQSYSTPLT | 89-97 | 6 |

Additional numbering system based on Kabat numbering is summarized in Table 3 below.

TABLE 3

| CDR | Kabat Sequence | Kabat position | SEQ ID NO: |
|---|---|---|---|
| HCDR1 | SYAMS | 31-35 | 7 |
| HCDR2 | SISRTGYTYYAESVKG | 50-65 | 2 |
| HCDR3 | VGTAFDY | 98-104 | 3 |
| LCDR1 | RASQSISSYLN | 24-34 | 4 |
| LCDR2 | AASSLQS | 50-56 | 5 |
| LCDR3 | QQSYSTPLT | 89-97 | 6 |

Additional numbering system based on Chothia is presented in Table 4 below.

TABLE 4

| CDR | Chothia Sequence | Chothia Position | SEQ ID NO: |
|---|---|---|---|
| HCDR1 | GFTFSSY | 26-32 | 8 |
| HCDR2 | SRTGY | 51-57 | 9 |
| HCDR3 | VGTAFDY | 98-104 | 3 |
| LCDR1 | RASQSISSYLN | 24-34 | 4 |
| LCDR2 | AASSLQS | 50-56 | 5 |
| LCDR3 | QQSYSTPLT | 89-97 | 6 |

Therefore, in a specific aspect, the invention relates to an anti-Nrp1A antibody or an antigen-binding fragment thereof comprising:
  a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3); or
  a heavy chain variable region comprising the amino acid sequence of SEQ ID NO: 7 (H-CDR1); the amino acid sequence of SEQ ID NO: 2 (H-CDR2); and the amino acid sequence of SEQ ID NO: 3 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3); or a heavy chain variable region comprising the amino acid sequence of SEQ ID NO: 8 (H-CDR1); the amino acid sequence of SEQ ID NO: 9 (H-CDR2); and the amino acid sequence of SEQ ID NO: 3 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

The anti-Nrp1A antibody of the present invention binds with high affinity to human Nrp1A. In an embodiment relating to this aspect, the anti-Nrp1A antibody of the present invention binds to human Nrp1A at a $K_D<50$ nM. In another embodiment, the anti-Nrp1A antibody of the present invention binds to human Nrp1A at a $K_D<15$ nM, as exemplified in Example 8.

The anti-Nrp1A antibody of the invention also binds to cyno-Nrp1A, mouse Nrp1A, rat Nrp1A and gerbil Nrp1A.

The high binding affinity of the antibody of the invention contributes to prolong the time for neutralization of Nrp1A after intravitreal injection and further allows a reduced injection frequency. A higher binding affinity further allows the administration of a lower dose, limiting the potential side effects. The improved binding affinity and reduced injection frequency considerably ameliorate the efficacy of the treatment of patients in need thereof. It also provides valuable benefits for the patient, especially an improved drug observance and compliance.

The anti-Nrp1A antibody of the present invention prevents Sema3A-induced cytoskeletal collapse in retinal cells with a functional potency of less than 130 pM, preferably less than 110 pM, more preferably less than 100 pM. In a preferred embodiment, the anti-Nrp1 antibody of the present invention prevents Sema3A-induced cytoskeletal collapse in retinal cells with a functional potency of 98 pM, as exemplified in Example 4. The results illustrate the efficiency of the antibody of the invention to inhibit the vasorepulsion induced by Sema3A.

The anti-Nrp1A antibody of the present invention further inhibit the permeability of the blood retinal barrier induced by VEGF-A with a functional potency of less than 4 nM, preferably less than 3 nM, more preferably less than 1 nM. In a preferred embodiment, the anti-Nrp1A antibody of the present invention prevents VEGF-induced loss of retinal cell integrity with a functional potency of 0.74 nM, as exemplified in Example 5. The results illustrate the efficiency of the antibody of the invention to inhibit the permeability of the blood retinal barrier induced by VEGF-A.

In a further aspect, the anti-Nrp1A antibody of the present invention proved to have a low immunogenicity risk as described in Example 9. This relies on an in silico prediction of the immunogenicity of the antibody. The immunogenicity risk is typically assessed by various methods well known such as by computer algorithm for predicting T cell epitopes, a major immunogenicity-influencing factor. It has been indeed reported that sequences containing T-cell epitopes present in proteins of interest could be predicted by using an algorithm based on a computational matrix approach, available under the name EpiMatrix (produced by EpiVax). The person skilled in the art may refer to Van Walle et al., Expert Opin Biol Ther. 2007 March; 7(3): 405-18 and Jawa and al., Clin Immunol. 2013 December; 149(3):534-55.

The antibody of the invention differs from therapeutic approaches based on targeting Sema3. Indeed, the antibody according to the invention inhibits the permeability of the blood retinal barrier induced by VEGF, preferably VEGF-A, while this effect is not observed with compounds targeting Sema3A. Therefore, the anti-Nrp1A therapeutic approach based on the antibody of the invention has the advantage to:
  inhibit the vasorepulsive effect of Sema3A;
  inhibit the permeability of the blood retinal barrier induced by Sema3A; and
  inhibit the permeability of the blood retinal barrier induced by VEGF-A.

The antibody of the invention differs from therapeutic approaches based on VEGF inhibition. Indeed, the antibody of the invention inhibits the binding of Sema3A to Nrp1, leading to the inhibition of the vasorepulsion induced by Sema3A, eventually to improving revascularisation especially in patients suffering from DMI.

In addition, the inventors have compared the potency of the antibody of the invention in comparison with inter alia Avastin®, Eylea® and Lucentis® in a VEGF Induced Cell Integrity Loss Assay as illustrated in Example 5. Avastin®, Eylea® and Lucentis® all target VEGF, while the antibody of the invention targets the A domain of Nrp1. It is noteworthy that the potency of the antibody of the invention in the VEGF-Induced Cell Integrity Loss Assay is similar to the potency of Avastin® and Eylea®, and better than the potency of Lucentis®. The inventors have thus developed an antibody that:
  prevents the binding of Nrp1 and Sema3A, so as to inhibit the vasorepulsion and the induction of the permeability of the blood retinal barrier by Sema3A, and
  surprisingly impacts the permeability of the blood retinal barrier induced by VEGF-A.

The inventors have illustrated that the antibody of the invention shows more advantageous properties than other antibodies or fragments targeting Nrp1 mentioned in the prior art and described herein in Example 3. Said further antibodies target different epitopes on Nrp1. The inventors have compared the properties of the antibody according to the invention and:
  an antibody directed against the A-domain of Nrp1 (YW64.3); and
  an antibody directed against the B-domain of Nrp1 (YW107.4.87).

The inventors have shown that the antibody of the invention is effective in a Sema3A induced cytoskeletal collapse assay, whereas YW107.4.87 is not (Example 4). These results illustrate that the antibody of the invention inhibits the vasorepulsion induced by Sema3A, leading to improved properties for revascularization, in particular in patients suffering from DMI.

The inventors have further shown that the antibody of the invention has an improved thermal stability compared to YW64.3, as measured by DSC (Example 11). These results illustrate that the antibody of the invention remains in its native and active conformation at physiological temperature. It is noteworthy that a higher thermal transition midpoints ($T_m$) reflects an improved stability of a protein at lower temperatures. The inventors have thus shown that the antibody of the invention shows improved thermal stability property contributing to an improved therapeutic efficacy while allowing a reduced injection dose and frequency to patients. In addition, a $T_m$ is indicative of a higher shelf-life and improved stability in time of the therapeutic product.

Humanization and Amino Acid Sequence Variants

Further variant anti-Nrp1A antibodies and antibody fragments can be engineered based on the set of CDRs identified under the sequences depicted in SEQ ID NO: 1 to 6. It is to be understood that in said variant anti-Nrp1A antibodies and antibody fragments the amino acid sequence of the CDRs remain unchanged but the surrounding regions e.g. FR regions can be engineered. Amino acid sequence variants of the anti-Nrp1A antibody can be prepared by introducing appropriate nucleotide changes into the anti-Nrp1A antibody DNA, or by peptide synthesis. Such variants include, for example, deletions from, and/or insertions into and/or substitutions of, residues within the amino acid sequences of the anti-Nrp1A antibodies of the examples herein. Any combination of deletions, insertions, and substitutions is made to arrive at the final construct, provided that the final construct possesses the desired characteristics. The amino acid changes also may alter post-translational processes of the humanized or variant anti-Nrp1A antibody, such as changing the number or position of glycosylation sites.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody.

In some aspects, the present invention includes nucleic acid molecules that encode the amino acid sequence variants of the anti-Nrp1A antibodies described herein. Nucleic acid molecules encoding amino acid sequence variants of the anti-Nrp1A antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-Nrp1A antibody.

In certain embodiments, the anti-Nrp1A antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')2 fragments (see, e.g., Carter et al., 1992, Bio/Technology 10:163-167). By another approach, F(ab')2 fragments can be isolated directly from recombinant host cell culture. Other techniques for the production of antibody fragments will be apparent to the skilled practitioner.

The anti-Nrp1A antibodies and antigen-binding fragments thereof can include modifications.

In certain embodiments, it may be desirable to use an anti-Nrp1A antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, the present invention includes covalent modifications of the anti-Nrp1A antibodies. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Epitope Binding

In a second aspect, the invention relates to an antibody that recognises a specific "Nrp1A epitope". In particular, the antibody of the invention binds to an epitope of the human Nrp1A as set forth in SEQ ID NO: 26.

In one aspect, the invention relates to an anti-Nrp1A antibody or an antigen-binding fragment thereof that binds to at least one amino acid residue within amino acid regions 68-77 of human Nrp1A as set forth in SEQ ID NO: 26.

In another aspect, the invention relates to an Nrp1A antibody or an antigen-binding fragment thereof that binds to the sequence depicted in SEQ ID NO: 27.

The sequences SEQ ID NO: 26 and 27 are depicted in Table 5 below.

TABLE 5

| Name | Sequence | | | | | SEQ ID NO: |
|---|---|---|---|---|---|---|
| Human Nrp1A | MERGLPLLCA SEKCEWLIQA GKFCGKIAPP YTTPSGVIKS PGGMFCRYDR | VLALVLAPAG PDPYQRIMIN PVVSSGPFLF PGFPEKYPNS LEIWDGFPDV | AFRNDKCGDT FNPHFDLEDR IKFVSDYETH LECTYIVFAP GPHIGRYCGQ | IKIESPGYLT DCKYDYVEVF GAGFSIRYEI KMSEIILEFE KTPGRIRSSS | SPGYPHSYHP DGENENGHFR FKRGPECSQN SFDLEPDSNP GILSMVFYTD | 26 |

TABLE 5-continued

| Name | Sequence | SEQ ID NO: |
|---|---|---|
| | SAIAKEGFSA NYSVLQSSVS EDFKCMEALG MESGEIHSDQ ITASSQYSTN WSAERSRLNY PENGWTPGED SYREWIQVDL GLLRFVTAVG TQGAISKETK KKYYVKTYKI DVSSNGEDWI TIKEGNKPVL FQGNTNPTDV VVAVFPKPLI TRFVRIKPAT WETGISMRFE VYGCKITDYP CSGMLGMVSG LISDSQITSS NQGDRNWMPE NIRLVTSRSG WALPPAPHSY INEWLQIDLG EEKIVRGIII QGGKHRENKV FMRKFKIGYS NNGSDWKMIM DDSKRKAKSF EGNNNYDTPE LRTFPALSTR FIRIYPERAT HGGLGLRMEL LGCEVEAPTA GPTTPLIGNLV DECDDDQANC HSGTGDDFQL TGOTTVLATE KPTVIDSTIQ SEFPTYGFNC EFGWGSHKTF CHWEHDNHVQ LKWSVLTSKT GPIQDHTGDG NFIYSQADEN QKGKVARLVS PVVYSQNSAH CMTFWYHMSG SHVGTLRVKL RYQKPEEYDQ LVWMAIGHQG DHWKEGRVLL HKSLKLYQVI FEGEIGKGNL GGIAVDDISI NNHISQEDCA KPADLDKKNP EIKIDETGST PGYEGEGEGD KNISRKPGNV LKTLDPILIT IIAMSALGVL LGAVCGVVLY CACWHNGMSE RNLSALENYN FELVDGVKLK KDKLNTQSTY SEA | |
| Nrp1A epitope | MINFNPHFDL | 27 |

As used herein, the term "Nrp1A epitope" refer to a molecule (e.g., a peptide) or a fragment of a molecule capable of binding to an anti-Nrp1A antibody or an antigen-binding fragment thereof. These terms further include, for example, a Nrp1A antigenic determinant recognized by any of the antibodies or antibody fragments of the present invention, which has a light and heavy chain CDR combination selected from heavy chain CDRs of the SEQ ID Nos: 1 to 3 and light chain CDRs of the SEQ ID NOs: 4 to 6.

Nrp1A antigen epitopes can be included in proteins, protein fragments, peptides or the like. The epitopes are most commonly proteins, short oligopeptides, oligopeptide mimics (i.e., organic compounds that mimic antibody binding properties of the Nrp1 antigen), or combinations thereof.

It has been found that the antibody of the invention binds to a unique epitope of the human Nrp1A. Preferably, said anti-Nrp1A antibody or antigen-binding fragment thereof binds to at least one amino acid residue within amino acid regions 68-77 of the extracellular domain of human Nrp1A, as set forth in SEQ ID NO: 26.

In the context of epitope binding, the phrase "binds within amino acid regions X-Y . . . " means that the anti-Nrp1A antibody or an antigen-binding fragment thereof binds to at least one, preferably all of the, amino acid residue within the amino acid region specified in the sequence.

In another aspect, the anti-Nrp1A antibody or the antigen-binding fragment thereof binds to at least 10%, 20%, 30%, 40%, 50%, 60%, 70%, 80%, 85%, 90%, 95%, or 100% of the amino acid sequence depicted in SEQ ID NO: 27. Preferably, the anti-Nrp1A antibody or the antigen-binding fragment thereof binds to the sequence depicted in SEQ ID NO: 27.

Therapeutic Uses

In a third aspect, the invention relates to an anti-Nrp1A antibody or an antigen-binding fragment thereof for use as a medicament.

As previously mentioned, Sema3A is the natural ligand to NRP1. More precisely, Sema3A binds to the A-domain of Nrp1. The inventors have exemplified that Semaphorin 3A is secreted by hypoxic retinal ganglion cells in ischemic/avascular retina and acts as a vasorepulsive cue. The inventors have confirmed that Sema3A indeed repels neovessels away from ischemic region by inducing a cytoskeletal collapse in these cells, thereby inhibiting vascular regeneration of the retina and enhancing pathologic preretinal neovascularization.

By targeting Nrp1, preferably the A-domain of Nrp1, the antibody of the invention prevents the binding of Nrp1 and Sema3A. The inventors have shown that modulating the vasorepulsive action with an Nrp1A-antibody increases the number of tip cells and redirect angiogenesis towards ischemic regions (Example 6), such as the pathologically enlarged foveal avascular zone in humans with diabetic macular ischemia.

In addition to preventing the binding of the A-domain of Nrp1 and Sema3A, the antibody of the invention shows the unexpected property of inhibiting the retinal permeability induced by VEGF, preferably VEGF-A. As previously mentioned, VEGF-A is a natural ligand to the B-domain of Nrp1. The antibody of the invention targets the A-domain of Nrp1 and does not specifically target the binding of Nrp1B and VEGF-A. However, the inventors observed that the antibody of the invention inhibits the permeability of blood retinal barrier induced by VEGF-A. Without wishing to being bound by theory, the inventors hypothesised that the inhibition of retinal permeability induced by VEGF-A by an antibody against the A-domain of Nrp1, preferably the antibody of the invention, is caused by sterical interference with the signaling holoreceptor complex consisting of Nrp1, VEGF receptor 2 and additional co-receptors.

VEGF-A is secreted among others by hypoxic astrocytes. VEGF-A is an important factor in the development of both proliferative DR and DME, altering retinal capillary permeability by modulating adherens junctions such as VE-Cadherin or tight-junctions such as occludins. VEGF-A stimulates endothelial cells to release matrix metalloproteinases (MMPs) and urokinase-type plasminogen activator, resulting in the degradation of basement membranes and making cell migration possible.

Therefore, the secretion of VEGF-A in hypoxic condition is an aggravating factor as it contributes to retinal permeability, worsening the macular edema. In addition, the inventors have shown that Sema3A and VEGF-A both promote vascular permeability by binding to Nrp1, leading to vascular leakage, thus contributing to macular edema.

The inventors have addressed this pathological situation by developing antibodies targeting Nrp1A, which proves highly helpful for:

redirecting angiogenesis towards ischemic regions, in order to improve revascularisation of the retina;

preventing pathological neovascularization of the vitreous region;

preventing blood retinal barrier breakdown induced by Sema3A; and preventing blood retinal barrier breakdown induced by VEGF-A.

Therefore, by combining two unexpected effects, the antibody of the invention proves to be highly beneficial for:

improving revascularisation of ischemic avascular region, typically in the retina of patients suffering from PDR, especially DMI;

preventing vascular leakage induced by the secretion of Sema3A, typically in patients suffering from PDR, especially DME; and preventing vascular leakage induced by the secretion of VEGF-A, typically in patients suffering from PDR, especially DME.

Consequently, the present invention provides an anti-Nrp1A antibody or an antigen-binding fragment thereof for use in the treatment or prevention of a retinal or eye disease.

It is noteworthy that the antibody according to the invention does not prevent the binding of VEGF and Nrp1 as illustrated in Example 12. The antibody of the invention does not affect VEGF-induced angiogenesis (as the antibody of the invention does not prevent VEGF-A induced endothelial cell proliferation) and only impacts the VEGF-A induced retinal permeability.

The inventors have indeed shown the antibody of the invention does not prevent endothelial cell proliferation as illustrated in Example 13. They further have shown that the antibody of the invention does not affect VEGF-induced angiogenesis in a VEGF-induced network formation assay (Example 14), as well as in laser induced choroidal neovascularization (Example 15). Therefore, the inventors confirmed that the antibody of the invention does not inhibit the angiogenesis induced by VEGF-A.

As explained throughout the disclosure of the invention, the antibody of the invention inhibits the vasorepulsive effect of Sema3A, hence allowing redirecting angiogenesis towards ischemic regions. In addition, the antibody of the invention prevents the blood retinal barrier breakdown induced by both Sema3A and VEGF-A. Despite its inhibitory effect on the permeability of the blood retinal barrier induced by VEGF-A, the antibody of the invention has surprisingly no effect on the angiogenesis induced by VEGF-A.

In addition, the antibody of the invention does not prevent revascularization. It would thus not impede the angiogenesis of ischemic regions. Therefore, the antibody of the invention is extremely helpful in clinical situation where the revascularisation is to be promoted, for example for improving revascularisation of ischemic avascular region, typically in the retina of patients suffering from PDR, especially DMI.

In a fourth aspect, the invention relates to an anti-Nrp1A antibody or an antigen-binding fragment thereof for use in the treatment or prevention of a disease selected from the group consisting of retinopathy, proliferative retinopathy such as retinopathy of prematurity, ischemic retinopathy, diabetic retinopathy including proliferative diabetic retinopathy and non-proliferative diabetic retinopathy, diabetic macular edema, diabetic macular ischemia, age-related macular degeneration, retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease.

The anti-Nrp1A antibody of the invention is in particular useful for treating or preventing diabetic retinopathy including proliferative diabetic retinopathy and non-proliferative diabetic retinopathy, ischemic retinopathy, diabetic macular edema, diabetic macular ischemia, age-related macular edema, retinal neovascularization and choroidal neovascularization.

In a preferred embodiment, said disease is diabetic macular ischemia and the antibody of the invention promotes vascular regeneration within the ischemic retina (revascularization) and prevents pathological neovascularization of the vitreous region of the eye.

In another preferred embodiment, said disease is diabetic macular edema and the antibody of the invention reduces permeability of the blood retinal barrier induced by Sema3A and VEGF-A.

In another preferred embodiment, the present invention provides an anti-Nrp1A antibody or an antigen-binding fragment thereof for inhibiting Sema3A-induced vasoregression from ischemic areas, inhibiting Sema3A-induced permeability of the blood retinal barrier and inhibiting VEGF-A induced permeability of the blood retinal barrier.

As used herein, the expression "inhibition of the permeability of the blood retinal barrier (BRB)", "inhibition of retinal permeability" and "inhibition of vascular permeability", can be used interchangeably and refer to the breakdown of the blood retinal barrier potentially leading to vascular leakage. Said vascular leakage can be induced by Sema3A on one hand and by VEGF, preferably VEGF-A, on the other hand. The inventors have now developed an antibody that can inhibit the permeability of the BRB induced by Sema3A as well as inhibit the permeability of the BRB induced by VEGF-A. The antibody of the invention thus prevents the breakdown of the blood retinal barrier, and prevents loss of retinal cell integrity induced by Sema3A and/or VEGF-A.

In a preferred aspect, the antibody of the invention is useful for the treatment of diabetic macular edema (DME) and/or diabetic macular ischemia (DMI). In a preferred embodiment, the antibody of the invention is useful for treating a patient suffering from DME and DMI. Preferably, the antibody of the invention is used for treating DMI as defined by over 15%, 20%, 25%, and more preferably 30% enlargement of foveal avascular zone (FAZ).

The invention proves extremely useful for patients suffering both from DMI and DME as the antibody of the invention inhibits retinal permeability induced by VEGF-A without impacting the pro-angiogenic effects that VEGF-A might have on vascular regeneration within ischemic retina.

In a fifth aspect, the present invention provides a pharmaceutical composition comprising an anti-Nrp1A antibody or an antigen-binding fragment thereof and a pharmaceutically acceptable carrier.

The anti-Nrp1A antibody or an antigen-binding fragment thereof is administered by any suitable means, including intravitreal, oral, parenteral, subcutaneous, intraperitoneal, intrapulmonary, and intranasal. Parenteral infusions include intramuscular, intravenous, intraarterial, intraperitoneal, or subcutaneous administration. In addition, the anti-Nrp1A antibody is suitably administered by pulse infusion, particularly with declining doses of the antibody. In one aspect, the dosing is given by injections, most preferably intravenous or subcutaneous injections, depending in part on whether the administration is brief or chronic. Preferably, the anti-Nrp1A antibody is administered through an intravitreal injection into the eye.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In a preferred embodiment, the dose range of the antibodies of the invention applicable per injection is usually from 1 mg/eye to 10 mg/eye, preferably between 1.5 mg/eye and 5 mg/eyes, more preferably between 2 mg/eye and 3 mg/eye and even more preferably about 2.5 mg/eye.

The term "suppression" is used herein in the same context as "amelioration" and "alleviation" to mean a lessening or diminishing of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the eye or retinal diseases addressed by the antibody of the invention.

The antibody need not be, but is optionally, formulated with one or more agents currently used to prevent or treat the disorder in question. The effective amount of such other agents depends on the amount of anti-Nrp1A antibody present in the formulation, the type of disorder or treatment, and other factors discussed above. These are generally used in the same dosages and with administration routes as used hereinbefore or about from 1 to 99% of the heretofore employed dosages.

Method of Treatment

In another aspect, the invention also encompasses any method for treating or preventing an eye or ocular diseases in a patient in need thereof, said method comprising the administration of an anti-Nrp1A antibody of the invention.

Preferably, the invention relates to a method of using an antibody according to the invention for inhibiting the vasorepressive effect of SemaA3. More preferably, the invention relates to said method for improving revascularisation of the retina.

Preferably, the invention relates to a method for treating or preventing an eye or a retinal disease comprising administering to a patient in need thereof a pharmaceutically effective amount of the antibody according to the invention. Preferably, said disease is selected from the group consisting of retinopathy, proliferative retinopathy such as retinopathy of prematurity, ischemic retinopathy, diabetic retinopathy including proliferative diabetic retinopathy and non-proliferative diabetic retinopathy, diabetic macular edema, diabetic macular ischemia, age-related macular degeneration, retinitis pigmentosa, inherited retinal dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease. More preferably, said disease is selected from the group consisting of diabetic retinopathy including proliferative diabetic retinopathy and non-proliferative diabetic retinopathy, ischemic retinopathy, diabetic macular edema, diabetic macular ischemia, age-related macular edema, retinal neovascularization, glaucoma and choroidal neovascularization. In a yet preferably embodiment, said disease is diabetic macular edema and/or diabetic macular ischemia.

All the disclosed technical features described herein are applicable to said method of treatment.

Pharmaceutical Compositions and Administration Thereof

A composition comprising an anti-Nrp1A antibody or an antigen-binding fragment thereof can be administered to a subject having or at risk of having an eye or retinal disease. The invention further provides for the use of an anti-Nrp1A antibody or an antigen-binding fragment thereof in the manufacture of a medicament for prevention or treatment of an Nrp1A related disease. The term "subject" as used herein means any mammalian patient to which an anti-Nrp1A antibody or an antigen-binding fragment thereof can be administered, including, e.g., humans and non-human mammals, such as primates, rodents, and dogs. Subjects specifically intended for treatment using the methods described herein include humans. The anti-Nrp1A antibody or an antigen-binding fragment thereof can be administered either alone or in combination with other compositions.

Various delivery systems are known and can be used to administer the anti-Nrp1A antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-Nrp1A antibody or an antigen-binding fragment thereof can be administered, for example by infusion, bolus or injection, and can be administered together with other biologically active agents. Administration can be systemic or local. In preferred embodiments, the administration is by intravitreal injection. Formulations for such injections may be prepared in, for example, prefilled syringes.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-Nrp1A antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-Nrp1A antibody or an antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-Nrp1A antibody or an antigen-binding fragment thereof that is effective in the treatment or prevention of an eye or retinal disease can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-Nrp1A antibody or an antigen-binding fragment thereof can be determined in cell cultures or experimental animals by standard pharmaceutical procedures for determining the $ED_{50}$ (the dose therapeutically effective in 50% of the population). An anti-Nrp1A antibody or an antigen-binding fragment thereof that exhibits a large therapeutic index is preferred.

The data obtained from the cell culture assays and animal studies can be used in formulating a range of dosage for use in humans. The dosage of the anti-Nrp1A antibody or an antigen-binding fragment thereof typically lies within a range of circulating concentrations that include the $ED_{50}$ with little or no toxicity. The dosage may vary within this range depending upon the dosage form employed and the route of administration utilized. For any anti-Nrp1A antibody or an antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

For intravitreal injection of the anti-Nrp1A antibody generally longer intervals between treatments are preferred. Due to its improved potency, the anti-Nrp1A antibody of the present invention can be administered in longer intervals.

In one embodiment the anti-Nrp1A antibody is administered every 6 weeks, preferably every 7 weeks, preferably every 8 weeks, preferably every 9 weeks, preferably every 10 weeks, preferably every 11 weeks, and more preferably every 12 weeks. In a yet preferred embodiment, the anti-Nrp1A antibody of the invention is administered once every 3 months.

Since the volume that can be administered to the eye is strictly limited, it is very important that the anti-Nrp1A antibody of the invention can be formulated to high concentrations. Furthermore, potency of the anti-Nrp1A antibody is of great importance as a potent antibody can exert its effect at even lower doses and thereby prolong activity and also intervals between treatments.

Antibodies of the present invention can be formulated to very high doses which include, but are not limited to 20 mg/ml, 30 mg/ml, 40 mg/ml, 50 mg/ml, 60 mg/ml, 70 mg/ml, 80 mg/ml, 90 mg/ml, or 100 mg/ml. Preferably, antibodies of the present invention can be formulated in a liquid formulation of about 50 mg/ml.

A typical dosage that can be administered to a patient is about 2.5 mg/eye. Typical buffer components that can be used for such a formulation comprise e.g. Sodium Acetate, PS20, and Trehalose Dihydrate.

In one embodiment, the anti-Nrp1A antibody is formulated with 10 mM histidine buffer, 240 mM sucrose, 0.02 w/v % polysorbate 20 at pH 5.5 with a final protein concentration of 60 mg/mL.

In some embodiments, the pharmaceutical compositions comprising the anti-Nrp1A antibody or an antigen-binding fragment thereof can further comprise a therapeutic agent, either conjugated or unconjugated to the binding agent.

With respect to therapeutic regimens for combinatorial administration, in a specific embodiment, the anti-Nrp1A antibody or the antigen-binding fragment thereof is administered concurrently with a therapeutic agent. In another specific embodiment, the therapeutic agent is administered prior or subsequent to administration of the anti-Nrp1A antibody or an antigen-binding fragment thereof, by at least an hour and up to several months, for example at least an hour, five hours, 12 hours, a day, a week, a month, or three months, prior or subsequent to administration of the anti-Nrp1A antibody or an antigen-binding fragment thereof.

Polynucleotides, Vectors, Host Cells, and Recombinant Methods

In a sixth aspect, the present invention encompasses isolated polynucleotides that comprise a sequence encoding an anti-Nrp1A antibody, vectors, and host cells comprising the polynucleotides, and recombinant techniques for production of the antibody. The isolated polynucleotides can encode any desired form of the anti-Nrp1A antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-Nrp1A antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-Nrp1A antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-Nrp1A antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-Nrp1A antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-Nrp1A antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-Nrp1 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-Nrp1A antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-Nrp1A antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Yeast enhancers also are advantageously used with yeast promoters.

Anti-Nrp1A antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding an anti-Nrp1A antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-Nrp1A antibody-encoding sequence, but is preferably located at a site 5' from the promoter.

Expression vectors used in eukaryotic host cells (yeast, fingi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-Nrp1A antibody. One useful transcription termination component is the bovine growth hormone polyadenylation region. See WO94/11026 and the expression vector disclosed therein. In some embodiments, anti-Nrp1A antibodies can be expressed using the CHEF system. (See, e.g., U.S. Pat. No. 5,888,809; the disclosure of which is incorporated by reference herein).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-Nrp1A antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-Nrp1A antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The anti-Nrp1A antibody of the invention can also be incorporated in viral vectors, i.e. the polynucleotide encoding for the anti-Nrp1A antibody or an antigen-binding fragment thereof is introduced into the viral vector and then expressed in the body of the patient after infection with the virus.

In another aspect, expression of anti-Nrp1A antibody is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for anti-Nrp1A antibody production and cultured in conventional nutrient media modified as appropriate for inducing promoters, selecting transformants, or amplifying the genes encoding the desired sequences.

The host cells used to produce anti-Nrp1A antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657, 866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an anti-Nrp1A or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-Nrp1A polypeptide (e.g., a heavy chain or light chain variable region), or its complement. Hybridizing nucleic acids of the type described herein can be used, for example, as a cloning probe, a primer, e.g., a PCR primer, or a diagnostic probe.

In one embodiment, the present invention relates to an isolated polynucleotide or polynucleotides comprising a sequence encoding a heavy chain as shown in SEQ ID NO: 18, SEQ ID NO: 20, SEQ ID NO: 21, SEQ ID NO: 22, SEQ ID NO: 23, SEQ ID NO: 24 or SEQ ID NO: 25 or a heavy chain variable region as shown in SEQ ID NO: 10, SEQ ID NO: 12, SEQ ID NO: 13, SEQ ID NO: 14, SEQ ID NO: 15, SEQ ID NO: 16 or SEQ ID NO: 17; and a sequence encoding a light chain as shown in SEQ ID NO: 19 or a light chain variable region as shown in SEQ ID NO: 11.

It is to be understood that in said anti-Nrp1A antibodies and antibody fragments the nucleic acid sequence coding for the CDRs remain unchanged (unchanged with respect to the amino acid they encode, equivalents of the DNA sequence due to the degeneracy of codons are possible) but the surrounding regions e.g. FR regions can be engineered.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-Nrp1A antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1: Upregulation of Sema3A in the Vitreous of DME and PDR patients

Figure 1B:
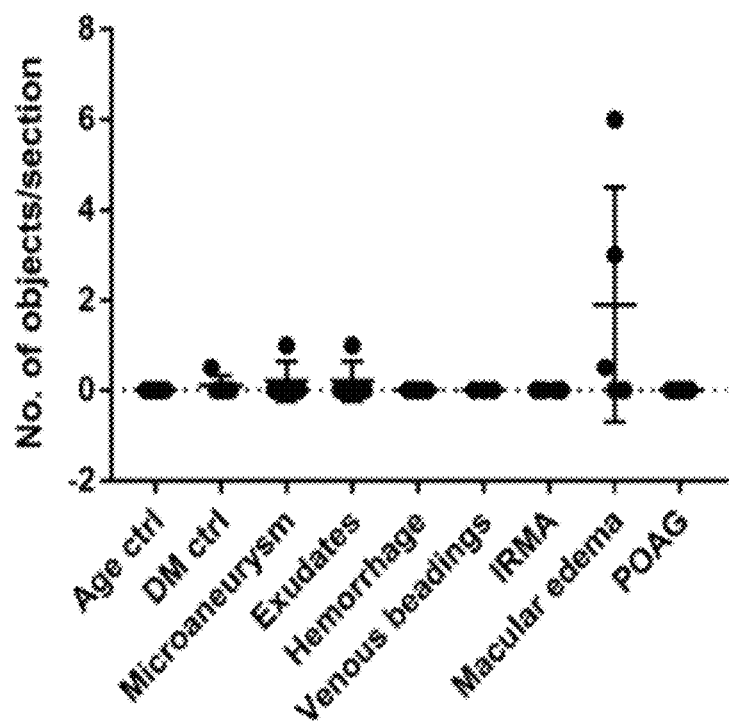

The expression of Sema3A in the retina of samples from human donors with a history of Diabetic Retinopathy was investigated by immunohistochemistry. The immunostaining protocol was as follows:
1. Thaw slides and let samples air dry for 30 min at room temperature (RT);
2. Draw pap pen box and let dry;
3. Antigen retrieval in 1% SDS for 5 min at RT;
4. Wash slides 3 times in PBS for 5 min;
5. Block sections in 1% BSA/0.3% Triton X100/PBS solution (blocking solution) for 30 min at RT;
6. Dilute rabbit-anti Sema3a (abcam, ab23393) 1st antibody 1:200 in blocking solution. Incubate sections on slide at RT overnight;
7. Rinse slides 3 times in PBS for 5 min;
8. 2nd antibody incubation with donkey anti-rabbit Alexa fluor546 (invitrogen, A10040) at 1:400 dilution in DAPI/0.3% Triton X100/PBS solution. Incubate sections on slide for 3 hours at RT;
9. Rinse slides 3-5 times in PBS for 5 min;
10. Coverslip sections with Aquamount and let air dry;
11. Image sections and grade intensity at 40× magnification. Sets of three sections per each human donor were immunostained for Sema3A. The Sema3A labelling was independently evaluated in each of these regions by observers previously trained for this specific task using a 5-point grading scheme (0=no detection, 1=low intensity, few spots, 2=moderate intensity, several spots, 3=bright intensity, widespread staining and 4=very bright intensity, abundant detection). The observers were unaware of the health status of the eye donors. Within the retina, Sema3A was associated with the vasculature wall of retinal blood vessels. The expression of Sema3A in retinal vasculature and retinal parenchyma was increased in patients with diabetic macular edema compared to diabetics without ocular pathology (FIG. 1).

Example 2: Inhibition of VEGF Induced Permeability

Permeability was measured in the retina of Brown Norway rats. Recombinant human VEGF-A (250 ng/2.5 µl) is injected intravitreally to induce hyperpermeability. Antibodies are injected at the same time as VEGF. Evans Blue dye (45 mg/ml) is intravenously injected 24 h after VEGF treatment into the Vena caudalis mediana (1 ml/kg). Eyes are enucleated 30 minutes later and fixated in formalin. A retinal flatmount is prepared and the Evans Blue fluorescence at 620 nm is measured using a confocal fluorescence microscope and image analysis software.

Figure 2:
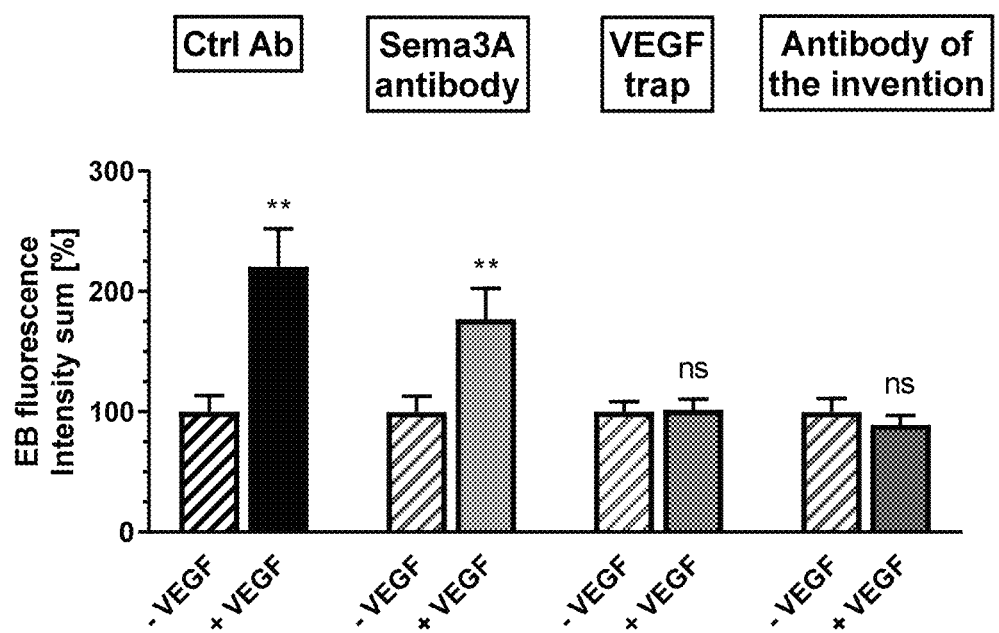
FIG. 2 shows the inhibition of VEGF-mediated effects— VEGF-A induced permeability in the retina of Brown Norway rats. Retinal Evans Blue fluorescence is used as a read-out for permeability to assess vascular leakage. Intravitreal injection of VEGF-A induces hyperpermeability in the retina. The antibody of the invention binding to the A-domain of Nrp1 inhibits VEGF-A-induced retinal permeability, similar to the VEGF trap (aflibercept). The antibody directed against the Nrp1 ligand semaphorin 3A (Sema3A antibody) does not inhibit VEGF-A-induced permeability in the retina.

The results are depicted in FIG. 2. The antibody of the invention completely inhibits the permeability induced by VEGF. This is similar to the results observed with VEGF trap aflibercept (Eylea®). An antibody against the Nrp1 ligand semaphorin 3A does not inhibit VEGF-A-induced permeability in the retina. This confirms that the antibody of the invention directed against the A-domain of Nrp1 inhibits VEGF-A-mediated effects and that this ability distinguishes it from an antibody directed against the Nrp1 ligand semaphorin 3A. The inventors have shown that an antibody directed against Sema3A completely inhibited the permeability induced by Sema3A, but not the permeability induced by VEGF-A. The inventors hypothesize that the inhibition of VEGF-A induced retinal permeability by an antibody against the A-domain of Nrp1 is caused by sterical interference with the signaling holoreceptor complex consisting of Nrp1, VEGF receptor 2 and additional co-receptors.

Example 3: Generation of Antibodies Directed Against Nrp1A and Nrp1B for Comparative Purposes For comparison purposes, the inventors have developed antibodies directed against Npr1A and Nrp1B respectively, as disclosed in WO2008143666 and WO2007056470. These antibodies include:
- an antibody directed against Nrp1A, referred to as "YW64.3"; and
- an antibody directed against Nrp1B, referred to as "YW107.4.87".

The anti-Nrp1A antibody is disclosed as clone "YW64.3" in WO2007056470 with the following features:
- the heavy chain variable domain is the sequence numbered 4 in WO2007056470, and
- the light chain variable domain is the sequence numbered 3 in WO2007056470.

The anti-Nrp1B antibody is disclosed as clone "YW107.4.87" in WO2007056470 with the following features:
- the heavy chain is the sequence numbered 6 in WO2007056470, and
- the light chain is the sequence numbered 5 in WO2007056470.

The sequences of YW64.3 and YW107.4.87 are summarised as follows in Table 6 below.

TABLE 6

| Name | Sequence | SEQ ID NO: |
| --- | --- | --- |
| YW64.3-HC | EVQLVESGGGLVQPGGSLRLSCAASGFSFSSEPISWVRQAPGKGLEW VSSITGKNGYTYYADSVKGRFTISADTSKNTAYLQMNSLRAEDTAVYYC ARWGKKVYGMDVWGQGTLVTVSSASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKRVEPKSCDKTHTCPPCPAPEAAGG PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMH EALHNHYTQKSLSLSPGK | 28 |

TABLE 6-continued

| Name | Sequence | SEQ ID NO: |
|---|---|---|
| YW64.3-LC | DIQMTQSPSSLSASVGDRVTITCRASQSISSYLAWYQQKPGKAPKLLIY GASSRASGVPSRFSGSGSGTDFTLTISSLQPEDFATYYCQQYMSVPITF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC | 29 |
| YW64.3-VH | EVQLVESGGGLVQPGGSLRLSCAASGFSFSSEPISWVRQAPGKGLEW VSSITGKNGYTYYADSVKGRFTISADTSKNTAYLQMNSLRAEDTAVYYC ARWGKKVYGMDVWGQGTLVTVSS | 30 |
| YW64.3-VL | DIQMTQSPSSLSASVGDRVTITCRASQSISSYLAWYQQKPGKAPKLLIY GASSRASGVPSRFSGSGSGTDFTLTISSLQPEDFATYYCQQYMSVPITF GQGTKVEIKR | 31 |
| YW107.4.87-HC | EVQLVESGGGLVQPGGSLRLSCAASGFTFSSYAMSWVRQAPGKGLE WVSQISPAGGYTNYADSVKGRFTISADTSKNTAYLQMNSLRAEDTAVY YCARGELPYYRMSKVMDVWGQGTLVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPS DIAVEWESNGQPENNYKTTPPVLDSDGSFFLYSKLTVDKSRWQQGNV FSCSVMHEALHNHYTQKSLSLSPGK | 32 |
| YW107.4.87-LC | DIQMTQSPSSLSASVGDRVTITCRASQYFSSYLAWYQQKPGKAPKLLIY GASSRASGVPSRFSGSGSGTDFTLTISSLQPEDFATYYCQQYLGSPPT FGQGTKVEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 33 |
| YW107.4.87-VH | EVQLVESGGGLVQPGGSLRLSCAASGFSFSYAMSWVRQAPGKGLEW VSQISPAGGYTNYADSVKGRFTISADTSKNTAYLQMNSLRAEDTAVYYC ARELPYYRMSKVMDVWGQGTLVTVSS | SEQ ID NO: 34 |
| YW107.4.87-VL | DIQMTQSPSSLSASVGDRVTITCRASQYFSSYLAWYQQKPGKAPKLLIY GASSRASGVPSRFSGSGSGTDFTLTISSLQPEDFATYYCQQYLGSPPT FGQGTKVEIKR | SEQ ID NO: 35 |

Example 4: Sema3A Induced Cytoskeletal Collapse Assay—Potency of the Antibody of the Invention in Sema3A-Induced Impedance Lowering and Comparison Between the Antibody of the Invention and Clones YW64.3 and YW107.4.87

Cellular activity of Nrp1 antibodies were assessed by a measure of cytoskeletal collapse in human retinal microvascular endothelial cells (HRMEC) using the XCELLigence response system (Real Time Cell Analysis Instruments, as commercialized by ACEA Biosciences). The system measures cell attachment, confluence and integrity via cellular impedance. HRMEC endogenously express Neuropilin-1 (Nrp1) and plexins, which are components of the class-3 Semaphorin holoreceptor. By binding to this receptor complex, semaphorins induce a collapse of F-actin fibers in the endothelium. In this functional assay, addition of recombinant Sema3A protein to a confluent layer of human retinal microvascular endothelial cells lowers cellular impedance due to the cytoskeletal collapse and subsequent shrinkage of the cells, measured as a reduction in cellular impedance.

Briefly, E-Plates were coated with Attachment Factor. Cells were seeded with a density of 20000 cells/well and were then allowed to grow into a monolayer under their normal growth conditions inside the XCELLigence device overnight. Sema3A with and without Nrp1 antibody combinations were added in the presence of 3 mM CaCl$_2$). The cell index was normalized to the time point before addition of substances. Calculations were done 5h after stimulation.

For determination of a functional potency and comparison between an exemplary antibody of the invention (clone I having the sequence depicted in SEQ ID NO: 10 as VH and the sequence depicted in SEQ ID NO: 11 as VL), clones YW64.3 and YW107.4.87 and antibody directed against Sema3A in the cytoskeletal collapse assay, Sema3A concentration response curves were combined with increasing concentrations of antibody as IC$_{50}$ shift experiments. A Gaddum Schild plot was performed to calculate the pA$_2$ value (the negative logarithm of the concentration of antibody needed to shift the Sema3A concentration response curve by factor 2). The potency in M was calculated from the pA$_2$ value as =POTENCY(10; –X), and disclosed in Table 7 below.

TABLE 7

| Potency in collapse assay (IC50 shift) | |
|---|---|
| Antibody of the invention | 98 pM |
| YW64.3 | 56 pM |
| YW107.4.87 | No effect |
| Antibody directed against Sema3A | 69 pM |

Example 5: VEGF Induced Cell Integrity Loss Assay—Potency of the Antibody of the Invention in VEGF-A-Induced Impedance Lowering and Comparison Between the Antibody of the Invention, Clones YW64.3 and YW107.4.87 and VEGF-Traps VEGF-A induces a loosening of cell-cell contacts that can be measured as a temporary impedance lowering in endothelial cells. The antibody of the invention prevents functional VEGF-A-induced impedance lowering. Cellular activity of Nrp1 antibodies to prevent VEGF-induced cell integrity loss were assessed by measuring impedance lowering in human retinal microvascular endothelial cells (HRMEC) using the XCELLigence system (Real Time Cell Analysis Instruments, as commercialized by ACEA Biosciences). HRMEC endogenously express Neuropilin-1 (Nrp1) and VEGFR2, components of the VEGF holoreceptor. VEGF-A induces a loosening of cell junctions between endothelial cells. In this functional assay, addition of recombinant VEGF-A protein to a confluent layer of human retinal microvascular endothelial cells lowers cellular impedance due to a loss of cell integrity.

Briefly, E-Plates were coated with Attachment Factor. Cells were seeded with a density of 20000 cells/well and were then allowed to grow into a monolayer under their normal growth conditions inside the XCELLigence device overnight. Culture medium was changed to a serum free medium containing 0.5% BSA for 3 hours before VEGF-A and antibodies were added. The cell index was normalized to the time point before addition of substances. Calculations were done at the VEGF-induced impedance minimum approximately 30 minutes after stimulation.

For determination of a functional potency, the EC50 of the antibody to prevent a loss of cell integrity induced by a fixed concentration of recombinant human VEGF-A was measured. A geometric mean value of the EC50 values of individual experiments was calculated. The results are summarised in Table 8 below for an exemplary antibody of the invention (clone I having the sequence depicted in SEQ ID NO: 10 as VH and the sequence depicted in SEQ ID NO: 11 as VL) and several comparatory molecules.

TABLE 8

| VEGF induced cell integrity loss IC50 (nM) | |
| --- | --- |
| Antibody of the invention | 0.74 |
| YW64.3 | 12.57 |
| YW107.4.87 | 13.74 |
| Avastin ® | 0.92 |
| Lucentis ® | 5.94 |
| Eylea ® | 0.33 |

Example 6: Effect of Anti-VEGF Treatment and Anti-Nrp1A on Tip Cell Density, Avascular Area and Pre-Retinal Tufts in Mouse OIR Model The effect of an exemplary antibody of the invention (clone I having the sequence depicted in SEQ ID NO: 10 as VH and the sequence depicted in SEQ ID NO: 11 as VL) on revascularization of ischemic avascular area was investigated in a mouse model of oxygen-induced retinopathy (OIR). Litters of C576BI/6J mice were exposed to an atmosphere of 75% oxygen from postnatal day 7 to postnatal day 12. This leads to a regression of blood vessels in the central retina and the formation of an avascular area. After returning to normoxic conditions, this area becomes ischemic. The pups receive a single intravitreal injection of 10 μg antibody in 0.5 μl solution in each eye under anaesthesia with isoflurane on postnatal day 12. On postnatal day 17, the animals are sacrificed and the eyes enucleated. Eyes are fixed in formalin and a retinal flatmount is prepared in which retinal blood vessels are stained with isolectin B4. The number of tip cells (specialized endothelial cells initiating the formation of new vessels) are counted at the avascular front along the whole retina (the boundary between vascularized peripheral area and avascular central area of the retina). The tip cells were identified by their special morphology showing filopodia extensions. For analysis, the number of tip cells is normalized to the length of the avascular front. The size of the avascular area is determined using a confocal microscope and image analysis software. The contralateral eye was used for histological sectioning of the eye cup and pre-retinal nuclei were counted.

Figure 3A:
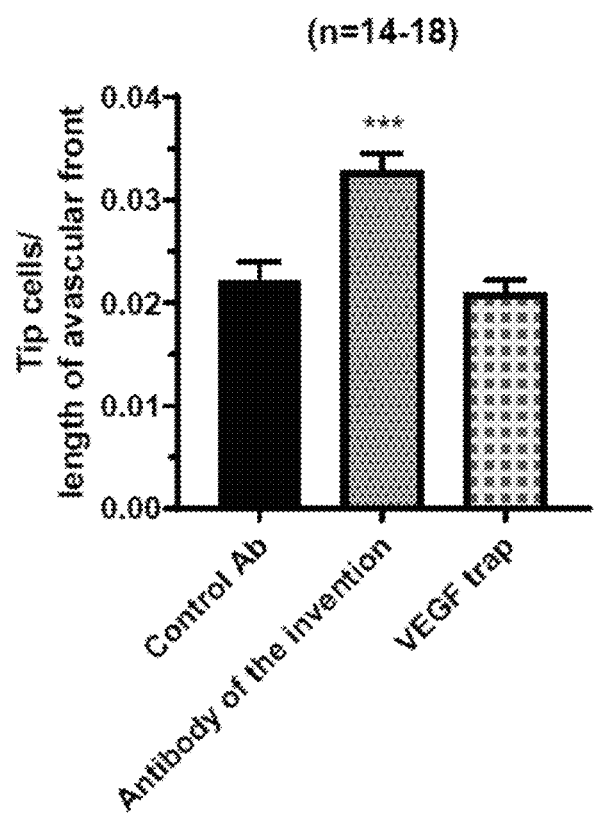
FIGS. 3A-3D show the effects of the antibody of the invention and anti-VEGF treatment on tip cell density, avascular area and pre-retinal tufts in mouse OIR model. Tip cell density, avascular area and pre-retinal neovascularization (tufts) were investigated in a model of oxygen-induced retinopathy in mouse pups. Animals were exposed 75% oxygen from P7 to P12 and received a single intravitreal injection of antibody after returning to normoxia on P12. A control antibody is directed against trinitrophenol. On P17, retinal flatmounts were prepared, stained with isolectin B4 and used for counting of tip cells and determination of the size of the retinal avascular area. The antibody of the invention binding to the A-domain of Nrp1 increases tip cell density and reduces avascular area whereas the VEGF trap aflibercept does not (FIG. 3A, FIG. 3C). The correlation between the tip cell density and avascular area is shown in (FIG. 3B). The contralateral eye was used for histological sectioning of the eye cup and pre-retinal nuclei were counted. Pre-retinal neovascularization was stronger inhibited by aflibercept than by the antibody of the invention (FIG. 3D).
Figure 3B:
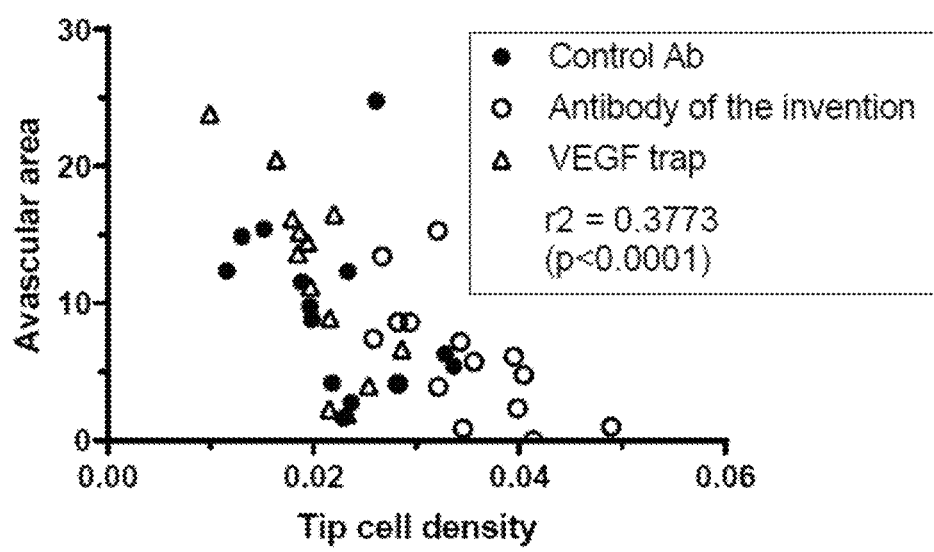
Figure 3C:
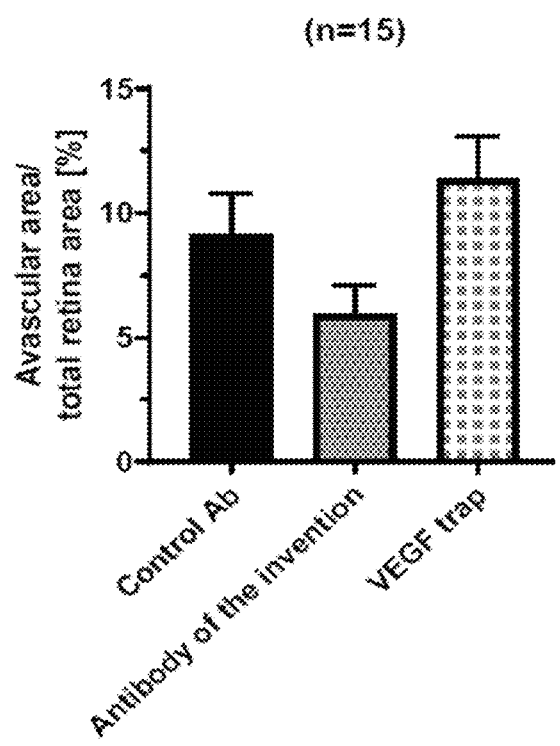
Figure 3D:
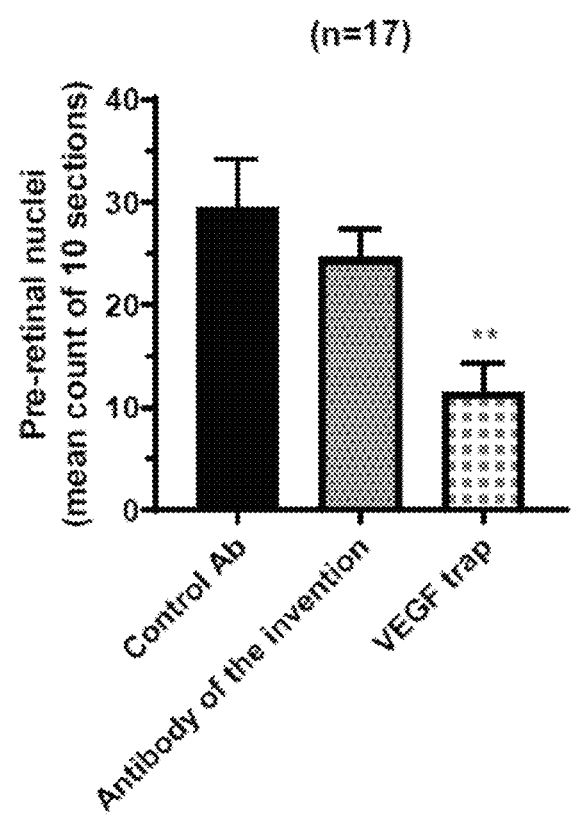

The antibody of the invention increases the tip cell density in the mouse OIR model (FIG. 3A). Furthermore, it shows a reduction of the avascular area (FIG. 3C). In contrast, the VEGF trap aflibercept (Eylea®) does neither increase tip cell density nor does it reduce avascular area. There is a negative correlation between the tip cell density and the size of the avascular area (FIG. 3B), indicating a mechanistic dependence of the two parameters. Overall, the antibody of the invention reduces ischemic avascular area size in an animal model of oxygen induced retinopathy, indicating a beneficial effect in Diabetic Macular Ischemia. Pathological neovascularization in the vitreous as evidenced by pre-retinal nuclei was inhibited by aflibercept while the antibody of the invention showed a moderate reduction of this pathological condition (FIG. 3D).

Example 7: Comparison of the Antibody of the Invention and Avastin t1/2 in Rabbit Eye The inventors have measured the half-life of an exemplary antibody of the invention (clone I having the sequence depicted in SEQ ID NO: 10 as VH and the sequence depicted in SEQ ID NO: 11 as VL) in various conditions. The results are summarised in Table 9 below.

TABLE 9

| Calculated t½ (day) | | |
| --- | --- | --- |
|  | According to the invention | Avastin |
| Vitreous | 4.8 | 4.4 |
| Retina | 3.5 | 4.8 |
| Aqueous | 4.5 | 4.5 |

The calculated half-lives were 4.8, 3.5 and 4.5 days in vitreous, retina, and aqueous humor respectively. These half-lives are similar to those reported in the literature for the clinically used recombinant humanized monoclonal IgG1 antibody Avastin (anti-VEGF, bevacizumab, Bakri et al., Opthalmology, 2007), which were also confirmed experimentally in-house. These results were as expected, since the intravitreal clearance of full length IgGs depends mainly on their molecular size, which is similar for the antibody of the invention and Avastin. Therefore, the human PK, including the ocular half-life of the antibody of the invention and Avastin® is expected to be similar. The reported human ocular half-life of Avastin® is 9.73±1.48 days (Hutton-Smith, 2016).

Example 8: Binding Affinity to Human Nrp1A

The inventors have assessed the binding affinity of an exemplary antibody of the invention (clone I having the sequence depicted in SEQ ID NO: 10 as VH and the sequence depicted in SEQ ID NO: 11 as VL).

The running buffer for this experiment and all dilutions (except where stated) were done in PBS-T-EDTA with 0.01% Tween20 [100 ul of 100% Tween20 was added to 2

L of PBS-T-EDTA to make final Tween 20 concentration of 0.01%]. The GLM sensorchip was normalized and pre-conditioned as per the manufacturer's recommendations. The sensorchip was activated with equal mixture of EDC/s-NHS in the horizontal direction for 300 sec at a flow rate of 30 µl/min and immobilized with Recombinant Protein A/G (6 µg/ml in 10 mM acetate pH 4.5) in the horizontal direction for 300 sec at a flowrate of 30 µl/min resulting in ~4370-4875 RU of Protein A/G on the surface. The sensorchip was deactivated with 1M ethanolamine HCl in the horizontal direction for 300 sec at a flowrate of 30 µl/min. The sensorchip was stabilized with 18 sec of 0.85% phosphoric acid at a flowrate of 100 µl/min 3 times horizontally and 3 times vertically.

The antibody of the invention (0.6 µg/ml) was captured on the Protein A/G surface vertically for 300 sec at a flowrate of 30 µl/min resulting ~1678 RU capture level. The baseline was stabilized by injecting PBS-T-EDTA for 60 sec at a flowrate of 100 µl/min horizontally with dissociation of 120 sec. The analyte was injected horizontally over the captured antibody for 300 sec at a flowrate of 30 µl/min and a dissociation for 1800 sec. The concentrations of the analytes were 0 nM, 6.25 nM, 12.5 nM, 25 nM, 50 nM, and 100 nM. The surface was regenerated by injecting 0.85% phosphoric acid for 18 sec at a flowrate of 100 µl/min one time horizontally and one time vertically. PBS-T-EDTA was injected for 60 sec at a flowrate of 100 µl/min one time vertically and one time horizontally.

The interspot (interactions with sensor surface) and blank (PBS-T-EDTA with 0.01% Tween20 or 0 nM analyte) were subtracted from the raw data. Sensorgrams were then fit globally to 1:1 Langmuir binding to provide on-rate (ka), off-rate (kd), and affinity ($K_D$) values.

The results are summarised in Table 10 below.

TABLE 10

| | Affinity ($K_d$) [nM] to human Nrp1 | | | |
|---|---|---|---|---|
| | Human | Cyno | Rat | Mouse | Gerbil |
| Antibody of the invention | 11.1 | 15.2 | 10.5 | 7.7 | 13.9 |

Example 9: Assessment of the Immunogenicity of the Antibody of the Invention

The inventors have assessed the predicted immunogenicity of an exemplary antibody according to the invention (clone I having the sequence depicted in SEQ ID NO: 10 as VH and the sequence depicted in SEQ ID NO: 11 as VL). For this purpose, the inventors have used an in silico tool for predicting such T cell epitopes (EpiMatrix developed by EpiVax).

By screening the sequences of many human antibody isolates, EpiVax has identified several highly conserved HLA ligands which are believed to have a regulatory potential. Experimental evidence suggests many of these peptides are actively tolerogenic in most subjects. These highly conserved, regulatory, and promiscuous T cell epitopes are known as Tregitopes (De Groot et al. Blood. 2008 Oct. 15; 112(8):3303-11). The immunogenic potential of neo-epitopes contained in humanized antibodies can be effectively controlled in the presence of significant numbers of Tregitopes.

For the purposes of antibody immunogenicity analysis, EpiVax includes a Tregitope-adjusted EpiMatrix Score and corresponding prediction of anti-therapeutic antibody response. To calculate the Tregitope-adjusted EpiMatrix Score, the scores of the Tregitopes are deducted from the EpiMatrix Protein Score. The Tregitope-adjusted scores have been shown to be well correlated with observed clinical immune response for a set of 23 commercial antibodies (De Groot et al. Clin Immunol. 2009 May; 131(2):189-201).

The results on the EpiMatrix scale are summarised in Table 11 below.

TABLE 11

| | Heavy Chain (% human) | | Epivax | Epivax | Light chain (% human) | |
|---|---|---|---|---|---|---|
| Molecule | FR | V-gene | (VH) | (Vκ) | FR | V-gene |
| Antibody of the invention | 90 | 88 | 10.02 | −3.12 | 100 | 96 |

Sequences of the antibody of the invention score on the low end of EpiMatrix scale, indicating that the antibody of the invention has a strongly limited potential for immunogenicity. Said EpiMatrix scale is well known by the person skilled in the art and can be found inter alia in FIG. 2 of the publication Mufarrege et al. Clin Immunol., 2017 March; 176:31-41.

Example 10: Comparison of Binding Affinity to Human Nrp1 of the Antibody of the Invention, YW64.3 and YW107.4.87

The inventors have assessed the binding affinity of an exemplary antibody of the invention (clone I having the sequence depicted in SEQ ID NO: 10 as VH and the sequence depicted in SEQ ID NO: 11 as VL) to human Nrp1 as well as the binding affinity of YW64.3 and YW107.4.87 to human Nrp1.

The running buffer for this experiment and all dilutions (except where stated) were done in PBS-T-EDTA with 0.01% Tween20 [100 ul of 100% Tween20 was added to 2 L of PBS-T-EDTA to make final Tween 20 concentration of 0.01%]. The GLM sensorchip was normalized and pre-conditioned as per the manufacturer's recommendations. The sensorchip was activated with equal mixture of EDC/s-NHS in the horizontal direction for 300 sec at a flow rate of 30 µl/min and immobilized with Recombinant Protein A/G (60 µg/ml in 10 mM acetate pH 4.5) in the horizontal direction for 300 sec at a flowrate of 30 µl/min. The sensorchip was deactivated with 1M ethanolamine HCl in the horizontal direction for 300 sec at a flowrate of 30 µl/min. The sensorchip was stabilized with 18 sec of 0.85% phosphoric acid at a flowrate of 100 µl/min 3 times horizontally and 3 times vertically.

The exemplary antibody of the invention and YW64.3 and YW107.4.87 were captured over the Protein A/G surface over 3 of 6 vertical channels. Human Nrp1A was prepared in PBS-T-EDTA buffer at concentrations of 100, 50, 25, 12.5, 6.25, and 0 nM. A PBS-T-EDTA buffer injection was used as a double reference for the kinetic data analysis. Each of the human Nrp1A solutions and PBS-T-EDTA buffer were injected simultaneously over the 6 horizontal channels for 5 min at a flow rate of 40 µL/min followed by 30 min dissociation phase. The surfaces were regenerated by an 18 sec injection of 0.85% Phosphoric acid at a flow rate of 100 µL/min followed by an injection of 60 sec PBS-T-EDTA at a flow rate of 100 µL/min. The interspot (interactions with sensor surface) and blank (PBS-T-EDTA with 0.01% Tween20 or 0 nM analyte) were subtracted from the raw data. Sensorgrams were then fit globally to 1:1 Langmuir binding to provide on-rate (ka), off-rate (kd), and affinity ($K_D$) values.

The Kinetic and affinity data of the antibody of the invention, YW64.3 and YW107.4.87 binding to human Nrp1 respectively are listed Table 12 below.

TABLE 12

| Sample Name | Kd to human Nrp1 |
| --- | --- |
| anti-Nrp1A (YW64.3) | 11.3 nM |
| anti-Nrp1B (YW107.4.87) | 37.5 nM |
| Antibody of the invention | 11.1 nM |

Example 11: Comparison of Protein Thermal Stability of the Antibody of the Invention and YW64.3

Differential scanning calorimetry (DSC) is a thermodynamic technique, which measures heat capacity as a function of temperature and constitute the most accurate method to assess the thermal stability of a protein conformation. DSC is widely used to assess protein thermal stability and conformational changes. The signal from a sample cell is compared with a reference cell lacking protein in an identical solution environment. As the temperature of the cells is increased, the temperature differences between the reference and sample cells are continuously measured and calibrated to power units. This data channel is referred to as the DP signal or the differential power between the reference and sample cells. The DP signal is converted to heat capacity. The heat capacity is continuously recorded as a function of temperature. After buffer subtraction and analysis of the resulting thermogram, the enthalpy and (apparent) thermal transition midpoints ($T_m$) for each transition can be obtained.

The temperature of protein unfolding ($T_m$) is tied to the stability of antibodies, specifically to aggregation during storage and long-term stability of the therapeutic product. The thermal transitions of monoclonal antibody $C_{H2}$ and $C_{H3}$ domains are typically invariant for different antibodies within an isotype, with the $C_{H2}$ domain unfolding prior to the $C_{H3}$ domain.

The inventors have compared the $T_m$ of:
- an antibody of the invention, more precisely "clone I" having the sequence depicted in SEQ ID NO: 10 as VH and the sequence depicted in SEQ ID NO: 11 as VL, and
- the clone YW64.3, as disclosed herein in Example 3, used for comparative purposes.

The thermal unfolding and aggregation of lead compound and YW64.3 at 1 mg/ml in 10 mM Histidine, pH 6.0 were monitored from 25° C. to 110° C. at a scan rate of 60° C./h via automated capillary differential scanning calorimetry (MicroCal, LLC). The data were analyzed using Origin 7.0 software (Origin-Lab). All thermograms were baseline-corrected and fitted using the 2-state model in Origin to obtain the apparent midpoint temperatures ($T_m$) for unfolding.

Melting curves of lead compound and YW64.3 are disclosed in Table 13 below.

TABLE 13

| | Tm1 (° C.) | Tm2 (° C.) | Tm3 (° C.) |
| --- | --- | --- | --- |
| Antibody of the invention | 68.33 | 83.23 | 89.70 |
| Clone YW64.3 | 68.50 | 81.96 | 84.65 |

For the antibody of the invention in 10 mM Histidine, pH 6, the first $T_m$ occurred at 68.33° C., this likely corresponds to the unfolding of the $C_{H2}$ domain. The two additional $T_m$'s, 83.23° C. and 89.70° C., correspond to the $C_{H3}$ domain and the Fab region, respectively. Similarly, for YW64.3, $C_{H2}$ domain unfolds at 68.5° C. followed by $C_{H3}$ at 81.96° C. and finally the Fab domain at 84.65° C. Therefore, the Fab unfolding temperature is about 5° C. higher for the antibody of the invention compared to YW64.3.

A higher $T_m$ value means that fewer molecules populate the unfolded state at a given temperature. Thus, a higher $T_m$ value is beneficial for therapeutic protein drugs as a high $T_m$ value sustains the active conformation at physiological temperatures.

Example 12: The Antibody of the Invention does not Prevent the Binding of Nrp1 to VEGF The inventors have further shown that an exemplary antibody of the invention (clone I having the sequence depicted in SEQ ID NO: 10 as VH and the sequence depicted in SEQ ID NO: 11 as VL) can bind to human Nrp1, even with VEGF present and binding to Nrp1 in a competitive assay.

For this purpose, biotinylated Human Vascular Endothelial Growth Factor-165 (hVEGF165) was captured on a streptavidin sensor tip (Molecular Devices, LLC. San Jose Calif.) by dipping each sensor in a 10 ug/mL biotinylated hVEGF165 solution prepared in 1×kinetic buffer (Molecular Devices) for 2 minutes in a sample plate. The sensors were then moved to wells having 1×kinetic buffer to wash away any unbound molecules for 2 minutes. 100 nM of human Nrp1 prepared in 1×kinetic buffer was then captured via the hVEGF165 for 10 minutes. Finally, sensors were dipped into various concentrations of the antibody of the invention (100 nM and 400 nM) for 10 minutes.

Data from active sensors was compared to several controls including no hVEGF165 capture, no hNrp1 and no antibody.

Figure 4:
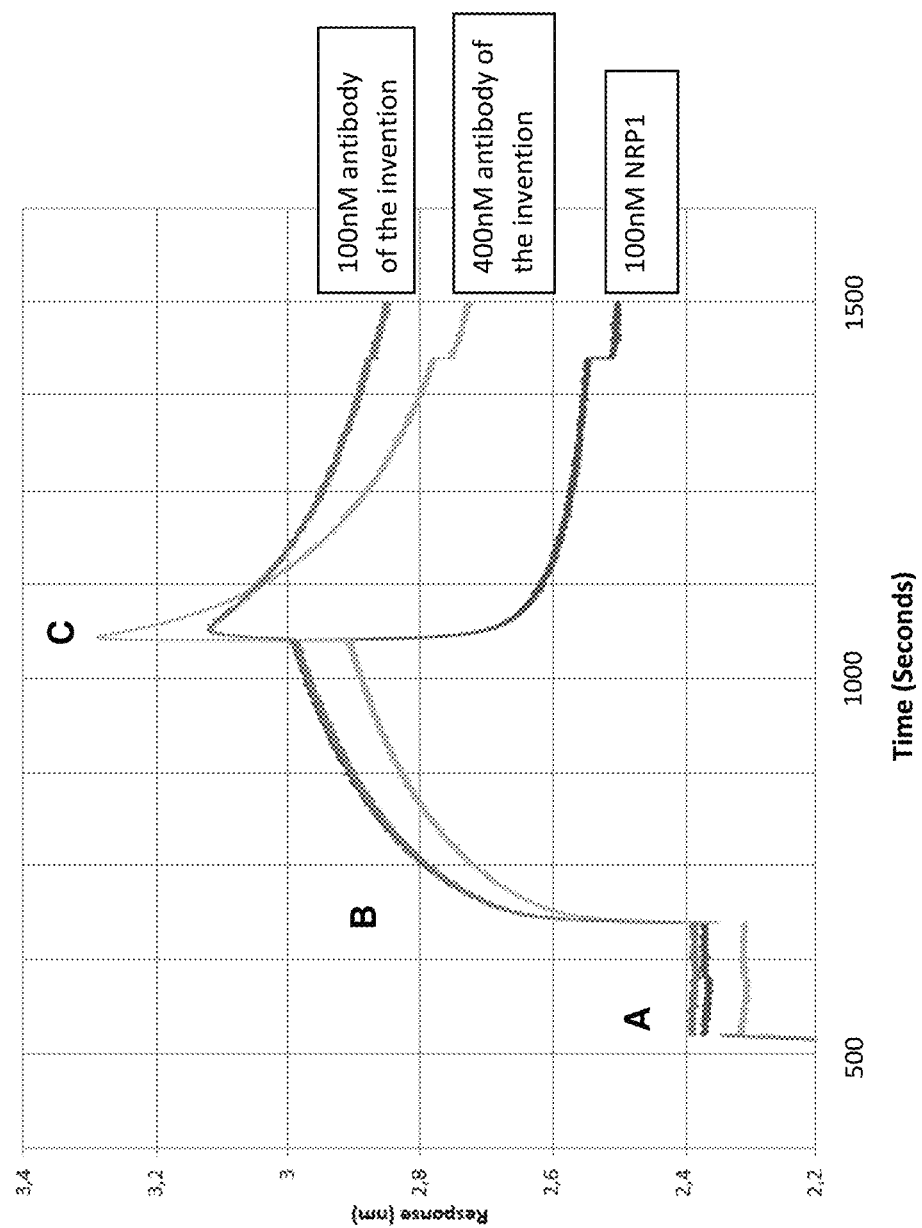
FIG. 4 shows the binding of the antibody of the invention to VEGF and Nrp1. The binding of the antibody of the invention to human Nrp1 (hNrp1) in the presence of Biotinylated Human Vascular Endothelial Growth Factor-165 (hVEGF165) was completed using Bio-Layer Interferometry (BLI). Biotinylated hVEGF165 was captured on a streptavidin sensor tip using 10 ug/ml biotin hNFAM1 (or buffer) (point A in FIG. 4). After washing sensor tips, 100 nM of human Nrp1 was captured via the hVEGF165 (point B in FIG. 4). Finally, sensors were dipped into various concentrations of the antibody of the invention (100 nM and 400 nM) to see if binding was observed (point C in FIG. 4). The results in FIG. 4 confirms that hNrp1 is bound to biotinylated hVEGF165.

The data show that the antibody of the invention can bind to human Nrp1, even with VEGF present and binding to Nrp1 (FIG. 4).

This indicates that the antibody of the invention does not prevent the binding of VEGF and human Nrp1.

Example 13: The Antibody of the Invention does not Prevent VEGF-A Induced Endothelial Cell Proliferation VEGF-A is one of the most important growth factors for endothelial cells that induces proliferation. Endothelial cell proliferation was investigated in human retinal microvascular endothelial cells (HRMEC) using the Incucyte system (Sartorius). In this functional assay, addition of recombinant VEGF-A protein to a subconfluent layer of HRMECs induces their proliferation.

Figure 5:
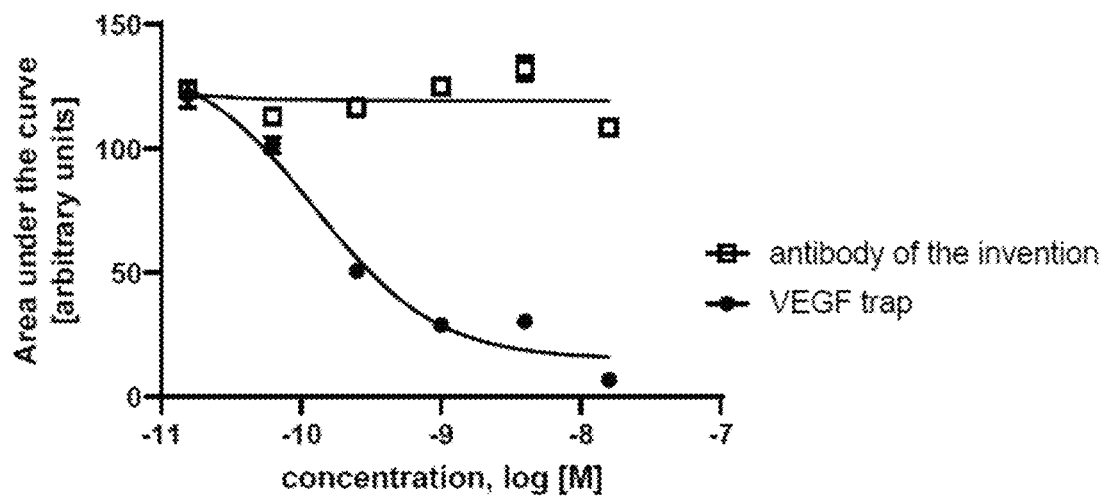
FIG. 5 shows VEGF-A induced endothelial cell proliferation of eendothelial cell (HRMEC). HMREC proliferation was investigated in human retinal microvascular endothelial cells using the Incucyte system (Sartorius). In this functional assay, addition of recombinant VEGF-A protein to a subconfluent layer of HRMECs induces their proliferation. The antibody of the invention does not prevent endothelial cell proliferation induced by VEGF-A, whereas VEGF trap aflibercept (Eylea®) shows a dose-dependent decrease in VEGF-A induced HRMEC proliferation.

Briefly, 96-well plates were coated with gelatine. Cells were seeded with a density of 3000 cells/well and were then allowed to attach in full endothelial growth medium for 18 hours. Cells were washed once with endothelial basal medium supplemented with 2% FCS and then cultured in the same medium for eight hours. VEGF-A and/or antibodies, including an examplary antibody of the invention (clone I having the sequence depicted in SEQ ID NO: 10 as VH and the sequence depicted in SEQ ID NO: 11 as VL) were added and cells were allowed to grow inside the Incucyte device. Phase contrast pictures were taken every 4 hours for a total of 96 hours. The images were used to evaluate the cell count. The cell count was normalized to the time point before addition of substances. The area under the curve was calculated from growth curves and baseline values were substracted (FIG. 5).

The inventors have shown that the antibody of the invention does not prevent endothelial cell proliferation induced by 10 ng/mL VEGF-A, whereas VEGF trap aflibercept (Eylea®) shows a dose-dependent decrease in VEGF-A induced HRMEC proliferation.

Example 14: VEGF-Induced Network Formation Assay—Efficacy of the Antibody of the Invention in VEGF-A-Induced Formation of Endothelial Network-Like Structures in a Co-Culture with Fibroblasts and Comparison Between the Antibody of the Invention and a VEGF-Trap VEGF-A is a key regulator of angiogenesis, potently inducing the growth of new blood vessels from pre-existing ones. Angiogenesis can be measured in vitro as the ability of endothelial cells to arrange in network-like structures, when cultured on top of a fibroblast cell layer. Network formation can be quantified after staining with the endothelial cell marker CD31.

The inventors have assessed and compared the ability to prevent VEGF-induced endothelial network formation of:
an exemplary antibody of the invention (clone I having the sequence depicted in SEQ ID NO: 10 as VH and the sequence depicted in SEQ ID NO: 11 as VL), and
an anti-VEGF antibody (bevacizumab, Avastin®).

More precisely, the cellular activity of said compounds to prevent VEGF-induced endothelial network formation was assessed by their capability to prevent the VEGF-A-induced formation of endothelial network structures in a co-culture with fibroblasts. HUVEC endogenously express Neuropilin-1 (Nrp1) and VEGFR2, components of the VEGF holoreceptor. In this functional assay, addition of recombinant VEGF-A protein to endothelial cells seeded on top of a confluent layer of fibroblasts increases the formation of endothelial networks.

Briefly, normal human dermal fibroblasts from juvenile foreskin (NHDF) were seeded in CellCarrier Ultra 96-well plates at a density of 25000 cells/well in a mixture of FGM-2 and EGM medium at equal parts. NHDFs were cultured under normal growth conditions for 7 days with one medium change. The medium was removed and human umbilical vein endothelial cells (HUVEC) were seeded at a density of 5000 cells/well in a 1/10 EGM/EBM mixture on top of the NHDFs.

HUVECs were allowed to attach in the incubator for 4 hours. The medium was removed and cells were then stimulated with recombinant human VEGF-A at a fixed concentration and the concentration response curves of the antibodies in 1/10 EGM/EBM medium. Cells were cultured for 7 days under normal culture conditions with a change to freshly prepared stimulation medium at day 3.

Cells were then fixed in 70% Ethanol/H$_2$O on ice for 30 min, followed by blocking for 30 min in DPBS+1% BSA. Endothelial cells were stained with a CD31 antibody (Miltenyi 130-108-038) for 60 min at room temperature. After washing for 3 times with DPBS, the 488-labeled secondary antibody (anti-mouse IgG PAb-A488 PLUS; Thermo A32723) and Hoechst were added and incubated for 60 min at room temperature in the dark. Cells were washed 3 times with DPBS. The plates were imaged using the Opera Phenix with a 5×air objective at the channels for AF488 and Hoechst. The Hoechst staining of the nuclei served only to confirm that cell layers were intact after the staining procedure, but was not included into the image analysis. The 488-positive network area per well was calculated using the Harmony 4.9 software.

For determination of a functional potency, the IC$_{50}$ of the antibodies to prevent an endothelial network formation induced by a fixed concentration of recombinant human VEGF-A was measured.

Figure 6:
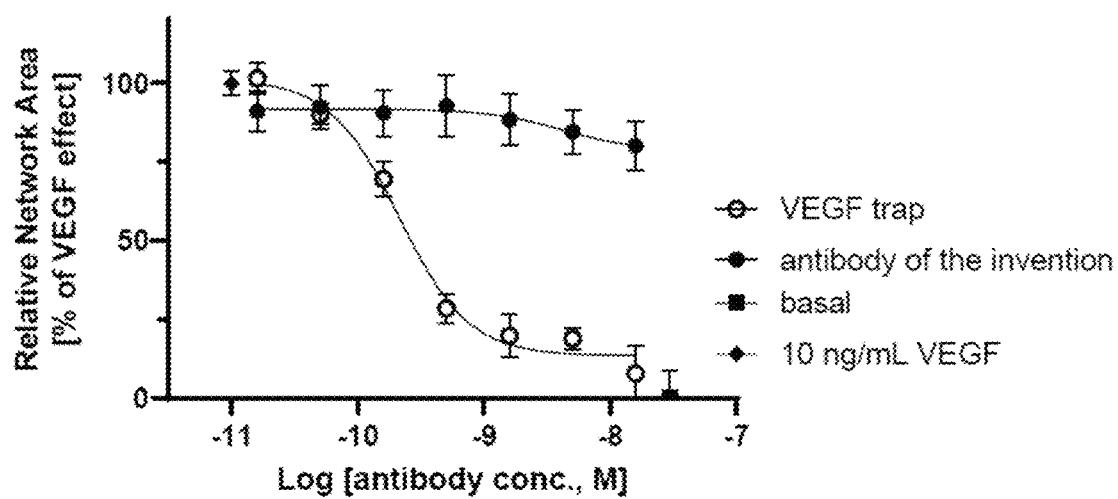
FIG. 6 shows the results of a VEGF-A induced endothelial network formation assay. In vitro angiogenesis was evaluated in a network formation assay in an endothelial/fibroblast co-culture. In this functional assay, VEGF-A induces the formation of endothelial networks on top of a confluent layer of fibroblasts. The efficacy and potency (IC50) of an exemplary antibody of the invention and a VEGF trap (bevacizumab, Avastin®) were evaluated to prevent 10 ng/mL VEGF-A-induced network formation. The antibody of the invention does not prevent endothelial network formation induced by VEGF-A, whereas VEGF trap (bevacizumab, Avastin®) shows a dose-dependent decrease in VEGF-A induced network formation.

The VEGF-A-induced network area was calculated (=mean VEGF-A-induced network area—mean basal network area) and set to 100%. The results are shown in FIG. 6.

The data are presented relative to the VEGF-A effect as mean±SD. A geometric mean value of the IC$_{50}$ values of individual experiments was calculated. The maximal efficacy was calculated at the highest antibody concentrations as percent inhibition of the VEGF-induced network area and the mean was calculated. The results are summarized in Table 14.

TABLE 14

| | Efficacy (percent inhibition) | Potency IC$_{50}$ (nM) |
|---|---|---|
| Antibody of the invention | 12.6 | not applicable |
| Avastin ® | 84.2 | 0.25 |

The inventors have shown that the antibody of the invention has no substantial effect on VEGF-A-induced in vitro angiogenesis. In contrast, the VEGF trap (bevacizumab, Avastin®) efficaciously and potently prevented VEGF-A induced network formation.

These results confirm the surprisingly and the unexpected property of the antibody of the invention which does not impact the VEGF-A-induced angiogenesis, while preventing the blood retinal barrier breakdown induced by VEGF-A.

Example 15: Laser Induced Choroidal Neovascularization in Brown Norway Rats—Efficacy of the Antibody of the Invention on Laser Induced Choroidal Neovascularization in Brown Norway Rats and Comparison Between the Antibody of the Invention and a VEGF Trap VEGF-A is a key regulator of angiogenesis, potently inducing the growth of new blood vessels from pre-existing ones. Angiogenesis can be measured in the eye in vivo as VEGF-A dependent choroidal neovascularization after generating lesions in the retinal pigment epithelium (RPE) and Bruch's membrane by laser photocoagulation. Neovascularization can be quantified after staining of lesions with isolectin B4 in flat mounts of RPE, choridea and sclera. This experimental in vivo model relies on laser injury to perforate Bruch's membrane, resulting in subretinal blood vessel recruitment from the choroid. This proves useful for testing test antiangiogenic therapies.

The inventors have assessed and compared the effects on laser induced choroidal neovascularization of:
- an exemplary antibody of the invention (clone I having the sequence depicted in SEQ ID NO: 10 as VH and the sequence depicted in SEQ ID NO: 11 as VL), and
- a VEGF trap (aflibercept, Eylea®).

Male Brown Norway rats (BN/Crl) with a body weight between 160 g and 180 g were obtained from Charles River Labs (Sulzfeld, Germany). Under anaesthesia, animals were placed in front of a fundus camera to position the optic nerve in the center of the image. Laser treatment was performed with a green Argon laser (Merilas) of 532 nm wavelength using a Micron IV system (Phoenix Research Laboratories, Pleasanton, Calif.).

The diameter of the laser beam was matched with the diameter of the optic nerve and laser pulses with an energy of 400 mW and a duration of 150 msec were used to generate 4 lesions per eye.

Lesions were placed between the large blood vessels with a distance from the optic nerve of about twice its diameter. A successful disruption of Bruch's membrane was recognized by the formation of bubbles immediately after the laser beam and confirmed by OCT scan.

For intravitreal injection, rats were anaesthetized by intraperitoneal injection of ketamine (67 mg/kg) and xylazin (6.7 mg/kg). Pupils were dilated by topical application of Mydrum eye drops and in addition, the animals received analgetic eye drops (Novesine 0.4%). Injection into the vitreous was done with a 34G Hamilton syringe at the *Ora serrata*. Each eye received two intravitreal injections of a volume of 5 μl. The first intravitreal injection was performed immediately after the laser treatment (within the same anaesthesia) on day 1, and the second intravitreal injection was performed on day 8.

Animals were sacrificed 14 days after laser treatment by cervical dislocation under anaesthesia. Eyes were enucleated and cut along the *Ora serrata*. Cornea, iris, lens, vitreous and retina were removed and the remaining eye cup (consisting of RPE, choroidea and sclera) was fixed in PFA (4%) for 1 h at 4° C. and then transferred to PBS containing 0.1% Triton X-100 for 1 h at 4° C. The eye cup was stained overnight in the dark at room temperature with FITC-labelled isolectin B4 (10 μg/ml in saline) and washed 3 times with PBS. The eye cup was transferred to a glass slide and cut four times to achieve a flat cloverleaf-like structure. The tissue was covered with mounting medium (Vectashield H-1200 containing DAPI) and a coverslip was put on top to obtain a RPE/choroidea/sclera flatmount (RPE side up). The samples were analyzed at a wavelength of 488 nm with a LSM 700 confocal laser scanning-microscope (Carl Zeiss, Jena) and lesion size was determined by image analysis.

Figure 7:
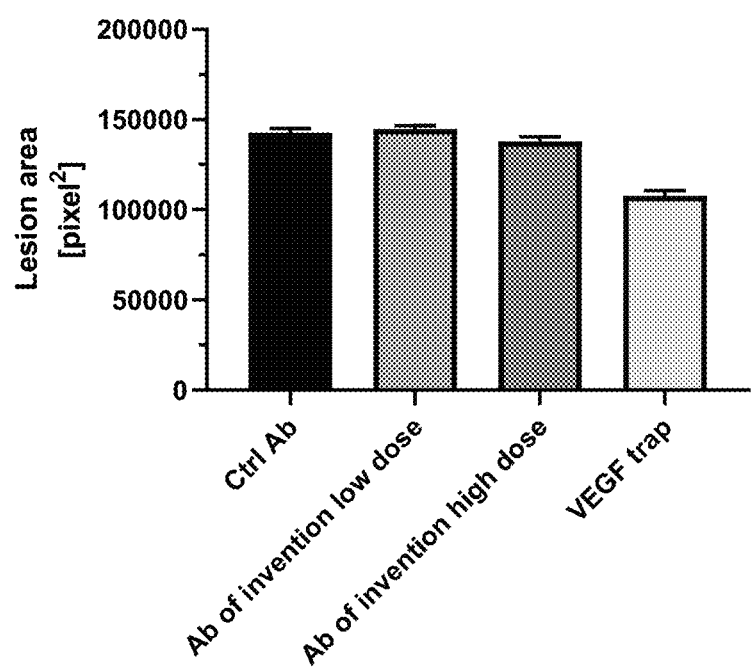
FIG. 7 shows the area of choroidal neovascular lesions in Brown Norway rats after ocular laser photocoagulation. Animals had received two intravitreal injections of IgG control antibody (109 μg/eye), antibody of the invention (low dose 54.5 mg/eye; high dose 109 μg/eye) or the VEGF trap Eylea® (200 μg/eye) on day 1 and day 8. Laser photocoagulation was performed on day 1 immediately before the first intravitreal injection. Lesion area was analyzed on day 15 by isolectin B4 staining of RPE/choroidea/sclera flatmounts. Data are mean±SEM. Statistical analysis was done by unpaired two-sided t-test (****, p<0.0001).

The results are shown in FIG. 7. The antibody of the invention had no effect on lesion area while the VEGF trap Eylea® reduced the lesion area by 24%. Therefore, the antibody of the invention did not affect VEGF-A dependent choroidal neovascularization in Brown Norway rats.

Said results confirm that the antibody of the invention does not inhibit the angiogenesis induced by VEGF-A. This confirm that the antibody of the invention is extremely helpful in clinical situation where the revascularisation is to be promoted, for example in patient suffering from diabetic macular ischemia who would benefit from a revascularisation of the retina.

As explained throughout the disclosure of this invention, the antibody of the invention inhibits the vasorepulsive effect of Sema3A, hence allowing redirecting angiogenesis towards ischemic regions. In addition, it prevents the blood retinal barrier breakdown induced by Sema3A on one hand and by VEGF-A on the other hand.

Despite its inhibitory effect on the permeability of the blood retinal barrier induced by VEGF-A, the antibody of the invention has surprisingly no effect on the angiogenesis induced by VEGF-A.

Consequently, as shown herein, the antibody of the invention does not prevent revascularisation, indicating that it would not impede the angiogenesis of ischemic regions. Therefore, these results confirm that the antibody of the invention is highly beneficial for improving revascularisation of ischemic avascular region, typically in the retina of patients suffering from PDR, especially DMI.

The invention claimed is:

1. An anti-Nrp1A antibody or an antigen-binding fragment thereof comprising:
a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

2. The anti-Nrp1A antibody or the antigen-binding fragment thereof according to claim 1, wherein the antibody or the antigen-binding fragment thereof comprises:
a heavy chain variable region comprising an amino acid sequence at least 95% identical to the amino acid sequence of SEQ ID NO: 10, SEQ ID NO: 12, SEQ ID NO: 13, SEQ ID NO: 14, SEQ ID NO: 15, SEQ ID NO: 16 or SEQ ID NO: 17; and
a light chain variable region comprising an amino acid sequence at least 95% identical to the amino acid sequence of SEQ ID NO: 11.

3. The anti-Nrp1A antibody or the antigen-binding fragment thereof according to claim 1, wherein the antibody or the antigen-binding fragment thereof comprises:
a heavy chain variable region comprising the amino acid sequences of SEQ ID NO: 10, SEQ ID NO: 12, SEQ ID NO: 13, SEQ ID NO: 14, SEQ ID NO: 15, SEQ ID NO: 16 or SEQ ID NO: 17; and
a light chain variable region comprising the amino acid sequence of SEQ ID NO: 11.

4. The anti-Nrp1A antibody or the antigen-binding fragment thereof according to claim 1, wherein the antibody or the antigen-binding fragment thereof comprises:
a heavy chain comprising the amino acid sequence of SEQ ID NO: 18, SEQ ID NO: 20, SEQ ID NO: 21, SEQ ID NO: 22, SEQ ID NO: 23, SEQ ID NO: 24 or SEQ ID NO: 25; and a light chain comprising the amino acid sequence of SEQ ID NO: 19.

5. The anti-Nrp1A antibody or the antigen-binding fragment thereof according to claim 4, wherein the antibody or the antigen-binding fragment thereof comprises:
   a. a heavy chain consisting of the amino acid sequence of SEQ ID NO: 18 and a light chain consisting of the amino acid sequence of SEQ ID NO: 19;
   b. a heavy chain consisting of the amino acid sequence of SEQ ID NO: 20 and a light chain consisting of the amino acid sequence of SEQ ID NO: 19;
   c. a heavy chain consisting of the amino acid sequence of SEQ ID NO: 21 and a light chain consisting of the amino acid sequence of SEQ ID NO: 19;
   d. a heavy chain consisting of the amino acid sequence of SEQ ID NO: 22 and a light chain consisting of the amino acid sequence of SEQ ID NO: 19;
   e. a heavy chain consisting of the amino acid sequence of SEQ ID NO: 23 and a light chain consisting of the amino acid sequence of SEQ ID NO: 19;
   f. a heavy chain consisting of the amino acid sequence of SEQ ID NO: 24 and a light chain consisting of the amino acid sequence of SEQ ID NO: 19; or
   g. a heavy chain consisting of the amino acid sequence of SEQ ID NO: 25 and a light chain consisting of the amino acid sequence of SEQ ID NO: 19.

6. The anti-Nrp1A antibody or the antigen-binding fragment thereof according to claim 1, wherein the antibody or the antigen-binding fragment thereof comprises:
   a. a heavy chain comprising the amino acid sequence of SEQ ID NO: 18 and a light chain comprising the amino acid sequence of SEQ ID NO: 19;
   b. a heavy chain comprising the amino acid sequence of SEQ ID NO: 20 and a light chain comprising the amino acid sequence of SEQ ID NO: 19;
   c. a heavy chain comprising the amino acid sequence of SEQ ID NO: 21 and a light chain comprising the amino acid sequence of SEQ ID NO: 19;
   d. a heavy chain comprising the amino acid sequence of SEQ ID NO: 22 and a light chain comprising the amino acid sequence of SEQ ID NO: 19;
   e. a heavy chain comprising the amino acid sequence of SEQ ID NO: 23 and a light chain comprising the amino acid sequence of SEQ ID NO: 19;
   f. a heavy chain comprising the amino acid sequence of SEQ ID NO: 24 and a light chain comprising the amino acid sequence of SEQ ID NO: 19; or
   g. a heavy chain comprising the amino acid sequence of SEQ ID NO: 25 and a light chain comprising the amino acid sequence of SEQ ID NO: 19.

7. A pharmaceutical composition comprising an antibody or an antigen-binding fragment according to claim 1 and a pharmaceutically acceptable carrier.

8. An anti-Nrp1A antibody comprising a heavy chain comprising the amino acid sequence of SEQ ID NO: 18 and a light chain comprising the amino acid sequence of SEQ ID NO: 19.

9. A pharmaceutical composition comprising an antibody according to claim 8 and a pharmaceutically acceptable carrier.

10. An anti-Nrp1A antibody comprising a heavy chain comprising the amino acid sequence of SEQ ID NO: 20 and a light chain comprising the amino acid sequence of SEQ ID NO: 19.

11. A pharmaceutical composition comprising an antibody according to claim 10 and a pharmaceutically acceptable carrier.

12. An anti-Nrp1A antibody comprising a heavy chain comprising the amino acid sequence of SEQ ID NO: 21 and a light chain comprising the amino acid sequence of SEQ ID NO: 19.

13. A pharmaceutical composition comprising an antibody according to claim 12 and a pharmaceutically acceptable carrier.

14. An anti-Nrp1A antibody comprising a heavy chain comprising the amino acid sequence of SEQ ID NO: 22 and a light chain comprising the amino acid sequence of SEQ ID NO: 19.

15. A pharmaceutical composition comprising an antibody according to claim 14 and a pharmaceutically acceptable carrier.

16. An anti-Nrp1A antibody comprising a heavy chain comprising the amino acid sequence of SEQ ID NO: 23 and a light chain comprising the amino acid sequence of SEQ ID NO: 19.

17. A pharmaceutical composition comprising an antibody according to claim 16 and a pharmaceutically acceptable carrier.

18. An anti-Nrp1A antibody comprising a heavy chain comprising the amino acid sequence of SEQ ID NO: 24 and a light chain comprising the amino acid sequence of SEQ ID NO: 19.

19. A pharmaceutical composition comprising an antibody according to claim 18 and a pharmaceutically acceptable carrier.

20. An anti-Nrp1A antibody comprising a heavy chain comprising the amino acid sequence of SEQ ID NO: 25 and a light chain comprising the amino acid sequence of SEQ ID NO: 19.

21. A pharmaceutical composition comprising an antibody according to claim 20 and a pharmaceutically acceptable carrier.

22. An anti-Nrp1A antibody or antigen-binding fragment thereof comprising a heavy chain variable region comprising the amino acid sequence of SEQ ID NO: 10 and a light chain variable region comprising the amino acid sequence of SEQ ID NO: 11.

23. A pharmaceutical composition comprising an antibody or antigen-binding fragment thereof according to claim 22 and a pharmaceutically acceptable carrier.

24. An anti-Nrp1A antibody or antigen-binding fragment thereof comprising a heavy chain variable region comprising the amino acid sequence of SEQ ID NO: 12 and a light chain variable region comprising the amino acid sequence of SEQ ID NO: 11.

25. A pharmaceutical composition comprising an antibody or antigen-binding fragment thereof according to claim 24 and a pharmaceutically acceptable carrier.

26. An anti-Nrp1A antibody or antigen-binding fragment thereof comprising a heavy chain variable region comprising the amino acid sequence of SEQ ID NO: 13 and a light chain variable region comprising the amino acid sequence of SEQ ID NO: 11.

27. A pharmaceutical composition comprising an antibody or antigen-binding fragment thereof according to claim 26 and a pharmaceutically acceptable carrier.

28. An anti-Nrp1A antibody or antigen-binding fragment thereof comprising a heavy chain variable region comprising the amino acid sequence of SEQ ID NO: 14 and a light chain variable region comprising the amino acid sequence of SEQ ID NO: 11.

29. A pharmaceutical composition comprising an antibody or antigen-binding fragment thereof according to claim 28 and a pharmaceutically acceptable carrier.

30. An anti-Nrp1A antibody or antigen-binding fragment thereof comprising a heavy chain variable region comprising the amino acid sequence of SEQ ID NO: 15 and a light chain variable region comprising the amino acid sequence of SEQ ID NO: 11.

31. A pharmaceutical composition comprising an antibody or antigen-binding fragment thereof according to claim 30 and a pharmaceutically acceptable carrier.

32. An anti-Nrp1A antibody or antigen-binding fragment thereof comprising a heavy chain variable region comprising the amino acid sequence of SEQ ID NO: 16 and a light chain variable region comprising the amino acid sequence of SEQ ID NO: 11.

33. A pharmaceutical composition comprising an antibody or antigen-binding fragment thereof according to claim 32 and a pharmaceutically acceptable carrier.

34. An anti-Nrp1A antibody or antigen-binding fragment thereof comprising a heavy chain variable region comprising the amino acid sequence of SEQ ID NO: 17 and a light chain variable region comprising the amino acid sequence of SEQ ID NO: 11.

35. A pharmaceutical composition comprising an antibody or antigen-binding fragment thereof according to claim 34 and a pharmaceutically acceptable carrier.

* * * * *